(12) United States Patent
Turner

(10) Patent No.: US 9,534,212 B2
(45) Date of Patent: Jan. 3, 2017

(54) HEAT-INACTIVATED COMPLEMENT FACTOR B COMPOSITIONS AND METHODS

(71) Applicant: WILLIAM MARSH RICE UNIVERSITY, Houston, TX (US)

(72) Inventor: Nancy A. Turner, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 14/631,263

(22) Filed: Feb. 25, 2015

(65) Prior Publication Data

US 2015/0175994 A1   Jun. 25, 2015

Related U.S. Application Data

(63) Continuation of application No. PCT/US2013/056609, filed on Aug. 26, 2013.

(60) Provisional application No. 61/693,633, filed on Aug. 27, 2012.

(51) Int. Cl.
| | |
|---|---|
| *C12N 9/50* | (2006.01) |
| *A61K 38/00* | (2006.01) |
| *C12N 9/64* | (2006.01) |
| *A61K 38/48* | (2006.01) |

(52) U.S. Cl.
CPC ............. *C12N 9/50* (2013.01); *A61K 38/00* (2013.01); *A61K 38/482* (2013.01); *C12N 9/6424* (2013.01); *C12Y 304/21047* (2013.01)

(58) Field of Classification Search
None
See application file for complete search history.

(56) References Cited

U.S. PATENT DOCUMENTS

2010/0120665 A1* 5/2010 Kaleko et al. .................. 514/8

FOREIGN PATENT DOCUMENTS

| WO | WO2004060817 | * | 7/2004 |
| WO | WO2011/058286 | * | 5/2011 |

OTHER PUBLICATIONS

WHO Technical Report, Guidelines on viral inactivation and removal procedures intended to assure the viral safety of human blood plasma products, Series No. 924, 2004.*
Zheng et al., Effect of plasma exchange on plasma ADAMTS13 metalloprotease activity, inhibitor level, and clinical outcome in patients with idiopathic and nonidiopathic thrombotic thrombocytopenic purpura, Blood, Jun. 1, 2004 vol. 103, No. 11.*
Soltis, R. et al. "The Effect of Heat Inactivation of Serum on Agregation of Immunoglobulins." 1979. Immunology, vol. 36, pp. 37-45; p. 37, Right Column, Second Paragraph; p. 38, Left Column, Third Paragraph.
Belogrudov, G. et al. "Factor B and Mitochondrial ATP Synthase Complex." Dec. 14, 2001. Journal of Biological Chemistry; vol. 277, pp. 6097-6103; p. 6098, Left Column, Fourth and Sixth Paragraphs. DOI: 10.1074.BC.M111256200.
Le, G. et al. "Profiling the Enzymatic Properties and Inhibition of Human Complement Factor B." Oct. 5, 2007. Journal of Biological Chemistry. vol. 282, pp. 34809-34816. Abstract. DOI: 10.1074/JBC. M705646200.
Chapin J, Weksler B, Magro C, Laurence J. Eculizumab in the Treatment of Refractory Idiopathic Thrombotic Thrombocytopenic Purpura. [Letter]. BR J Haematol. 2012;157 (6):772-774.
Waters AM, Licht C. Ahus Caused by Complement Dysregulation: New Therapies on the Horizon. Pediatric Nephrology. 2011;26 (1):41-57.
Hellstern P, Solheim BG. The Use of Solvent/Detergent Treatment in Pathogen Reduction of Plasma. Transfus Med Hemother. 2011;38 (1):65-70.

* cited by examiner

*Primary Examiner* — Suzanne M Noakes
*Assistant Examiner* — Stephen Chong
(74) *Attorney, Agent, or Firm* — Robert R. Riddle; Reed Smith LLP

(57) ABSTRACT

The present disclosure is directed to compositions comprising heat-inactivated complement factor B and methods of using the same to treat thrombotic or complement-mediated inflammatory disorders.

Figure 1A:
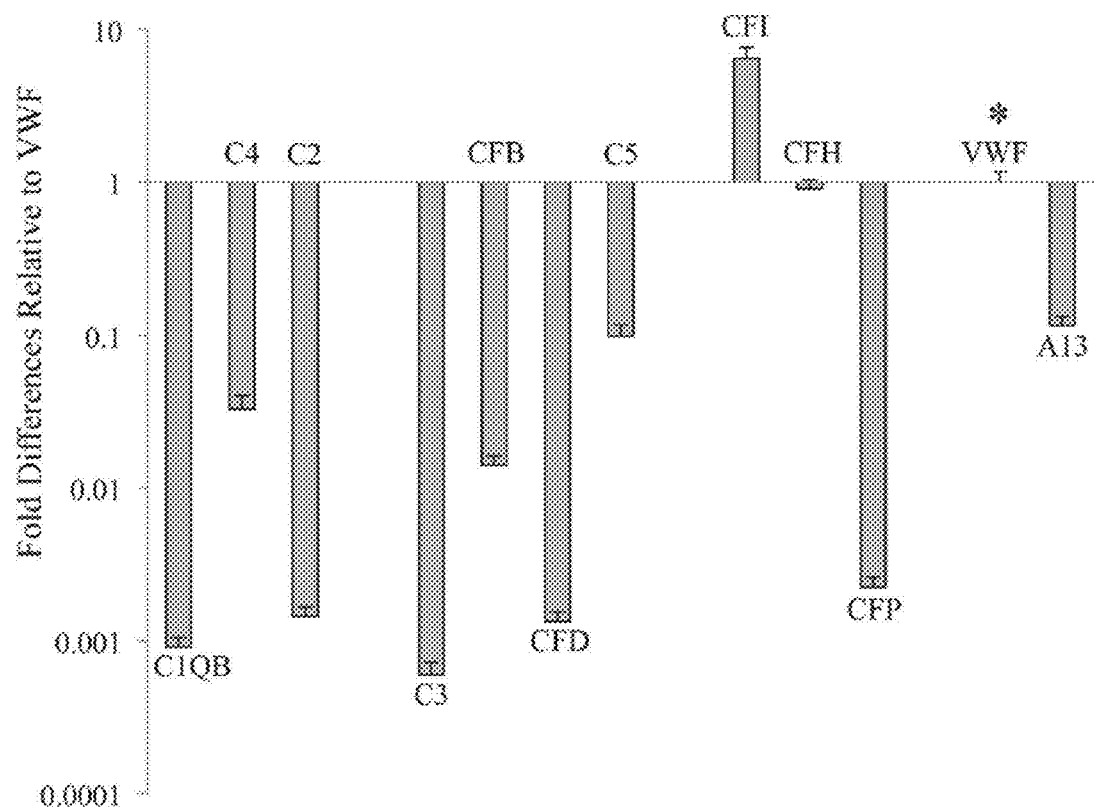

6 Claims, 36 Drawing Sheets
(26 of 36 Drawing Sheet(s) Filed in Color)

HEAT-INACTIVATED COMPLEMENT FACTOR B COMPOSITIONS AND METHODS

CROSS-REFERENCE TO RELATED APPLICATIONS

The present application is a continuation of PCT/US2013/056609 filed Aug. 26, 2013, which claims the benefit of U.S. Provisional Application Ser. No. 61/693,633 filed on Aug. 27, 2012, which is incorporated by reference.

BACKGROUND

The complement system helps or "complements" the ability of antibodies and phagocytic cells to clear pathogens from an organism. It is part of the immune system called the innate immune system that is not adaptable and does not change over the course of an individual's lifetime. However, it can be recruited and brought into action by the adaptive immune system. The complement system consists of a number of enzymes, proenzymes, and other proteins which form the principal effector mechanism of immunity in extracellular body fluids (especially blood plasma). When stimulated by one of several triggers, proteases in the system cleave specific proteins to release cytokines and initiate an amplifying cascade of further cleavages. The end-result of this activation cascade is massive amplification of the response and activation of the cell-killing membrane attack complex. Over 25 proteins and protein fragments make up the complement system, including serum proteins, serosal proteins, and cell membrane receptors. Three biochemical pathways activate the complement system: the classical complement pathway, the alternative complement pathway, and the lectin pathway.

Common clinical characteristics of the thrombotic microangiopathies (TMA), thrombotic thrombocytopenic purpura (TTP) and atypical hemolytic-uremic syndrome (aHUS), include microvascular platelet adhesion/aggregation/occlusion, thrombocytopenia, and mechanical hemolysis. Organ dysfunction in TTP is usually central nervous system, gastrointestinal or renal. In hemolytic-uremic syndrome (HUS), either shiga-toxin induced (D-HUS) or aHUS, organ dysfunction is predominantly renal. TTP is often associated with a deficiency of functional ADAMTS-13 (mutations or autoantibody-inhibited), the protease responsible for regulating the size of circulating von Willebrand factor (VWF) multimers. D-HUS results from infection of shiga-toxin harboring bacteria; and aHUS is developed from autoantibodies or defects in proteins of the alternative complement pathway (AP).

Endothelial cells (ECs) that line blood vessels produce and secrete into plasma: VWF, ADAMTS-13 and all the components of both the classical complement pathway (CP) and the AP. ECs store and secrete ultra-large (UL) von Willebrand factor (ULVWF) multimers with molecular masses over 10 thousand kDa and lengths up to 100 μm. The cell anchored ULVWF strings are hyper-adhesive to platelets and capable of producing microvascular thrombi before cleavage by ADAMTS-13 into less active smaller VWF forms. There is an accumulation of ULVWF strings on endothelial cell (EC) surfaces under conditions when the ULVWF strings are secreted at increased rates combined with lower amounts of functional ADAMTS-13. Bacterial toxins, inflammatory cytokines, phosphodiesterase inhibitors and calcium ionophore are among the agents that cause increased rates of ULVWF secretion from ECs. aHUS is the result of excessive complement activation or, more commonly, defective regulation of proteins of the AP. The primary effect of uncontrolled AP activity in aHUS is damage to renal endothelium, resulting in renal failure.

Although it has been established that AP regulation is dysfunctional in aHUS, it is unclear what initiates the AP activation. Limited activation of the AP can begin by direct hydrolysis of an intra-molecular bond in C3 to C3-$H_2O$. Subsequent cleavage activation of C3, releasing 9 kDa fragment C3a to form C3b, and further amplification of C3b production depends on the presence of "activating surfaces." C3b (not intact C3) attaches covalently via an exposed thioester to hydroxyl-containing amino acids (threonine, serine and tyrosine) on activating surfaces. C3b then binds factor B (FB) to produce C3bB. FB in the C3bB complex is cleaved to active Bb by factor D (FD) to produce C3bBb, the AP C3 convertase (with $t_{1/2}$ of 1-3 min) that is stabilized by factor P (properdin; FP). The Bb in C3bBb on an activating surface cleaves fluid-phase C3 to generate additional surface-bound C3b, a process that rapidly amplifies C3b generation from C3. As the ratio of C3b to Bb increases, C3bBbC3b is formed (as the AP C5 convertase), binds C5 with high affinity, and cleaves C5 to C5b. C5b combines with C6 and C7 to generate C5b67 complexes that insert into cell membranes. If C8 and multiple C9 molecules combine with C5b67 complexes in the cell membrane, then lytic C5b678(9)$_n$ terminal complement complexes (TCCs) are formed.

Factor H (FH) and factor I (FI) are fluid-phase negative regulatory proteins of the AP. FH can displace Bb from C3bBb and C3bBbC3b complexes and enables FI to cleave and inactivate C3b. Heterozygous mutations of the CFH gene or autoantibody-mediated inhibition of FH are prominent causes of aHUS. aHUS is also associated with heterozygous loss-of-function mutations of CFI, and heterozygous gain-of-function mutations in C3 or CFB.

In contrast to the AP, the CP and lectin-activated complement pathway (LP) are initiated by C1 (complex of C1$q_6$, C1$r_2$, C1$s_2$) attachment to antigen-antibody aggregates or mannose/N-acetylglucosamine-binding lectin (MBL)/MBL-associated protein (MASP), respectively. Both the CP and LP lead to cleavage and activation of C4 and C2 to generate C4b2a complexes. Analogous to activated C3b, activated C4b has an exposed thioester capable of binding covalently to surfaces. The C2a protease in C4b2a (the classical/lectin pathway C3 convertase) cleaves C3 into active C3b.

Human ECs of a variety of types (umbilical vein, arterial, lung microvascular, glomerular microvascular) secrete and anchor ULVWF strings in response to many stimuli. In vivo, EC-secreted/anchored ULVWF strings are exposed to all of the complement components in the circulation. After verifying and quantifying human umbilical vein endothelial cell (HUVEC) expression of complement proteins, we initially studied ULVWF strings and the attachment of complement components that were released exclusively from cultured ECs in the absence of other plasma proteins. ULVWF multimers are compressed in WPBs in a spring-like conformation that allows its rapid unfolding to the EC surface after stimulation, without additional application of shear stress or flowing conditions.

SUMMARY

Compositions and methods are provided for treating a complement-mediated inflammatory disorder. In one embodiment, a composition is provided comprising a heat-inactivated complement factor B. The composition may comprise heat-inactivated complement factor B in plasma or purified heat-inactivated complement factor B in a buffer.

In another embodiment, a method is provided comprising administering to an individual at risk for or suffering from a complement-mediated inflammatory disorder a composition comprising a heat-inactivated complement factor B. Examples of complement-mediated inflammatory disorders include thrombotic microangiopathies, age-related macular degeneration, lupus erythematosus, glomerulonephritis, paroxysmal nocturnal hemoglobinuria, and inflammatory bowel disease.

In yet another embodiment, a method for producing a producing a therapeutic composition is provided comprising obtaining a sample containing complement factor B, and heating the sample at a temperature from about 45° C. to about 56° C. for a period of from about 5 minutes to about 20 minutes. The sample can be a plasma sample such as, for example, normal human fresh frozen plasma, a cryosupernatant fraction of fresh frozen plasma, and normal human plasma. The method can further comprise the step of purifying complement factor B from the sample prior to or following the heating step.

DRAWINGS

The patent or application file contains at least one drawing executed in color. Copies of this patent or patent application publication with color drawing(s) will be provided by the Office upon request and payment of the necessary fee. A more complete understanding of this disclosure may be acquired by referring to the following description taken in combination with the accompanying figures.

FIG. 1A shows fold differences in gene expression of complement components in un-stimulated HUVECs relative to VWF expression (marked by asterisk). HUVECs were incubated for 24 hours in complete medium, followed by 24 hours in serum-free medium. Total RNA was extracted, reverse transcribed, and the cDNA was analyzed by real-time PCR using TAQMAN probes with GAPDH as the reference gene.

Figure 1B:
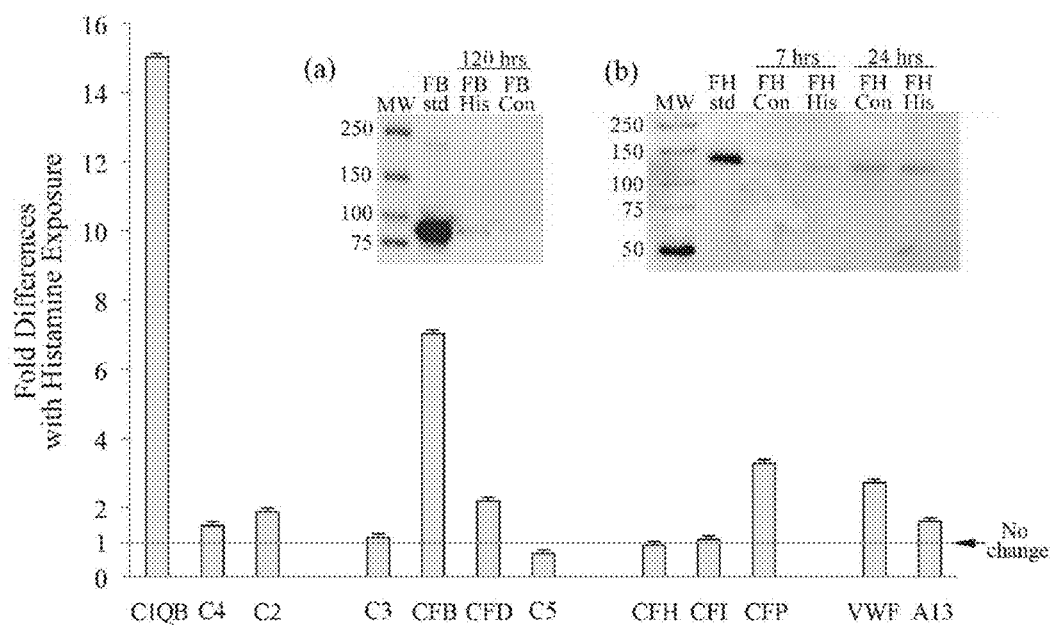

FIG. 1B shows fold differences in complement gene expression with histamine exposure. The line at 1 is the boundary between increased and decreased expression. Data shown are means plus standard deviations. Values for ADAMTS-13 are shown for comparison. Insets (a) and (b) show Western blot analysis of HUVEC conditioned serum-free media from un-stimulated control cells (Con) or from cells exposed to histamine (His): (a) FB detection; and (b) FH detection. HUVECs were incubated with 100 μM histamine for 24 hours in complete medium, followed by 24 hours in serum-free medium with histamine. Total RNA was extracted, reverse transcribed, and the cDNA was analyzed by real-time PCR using TAQMAN probes with GAPDH as the reference gene.

Figure 1C:
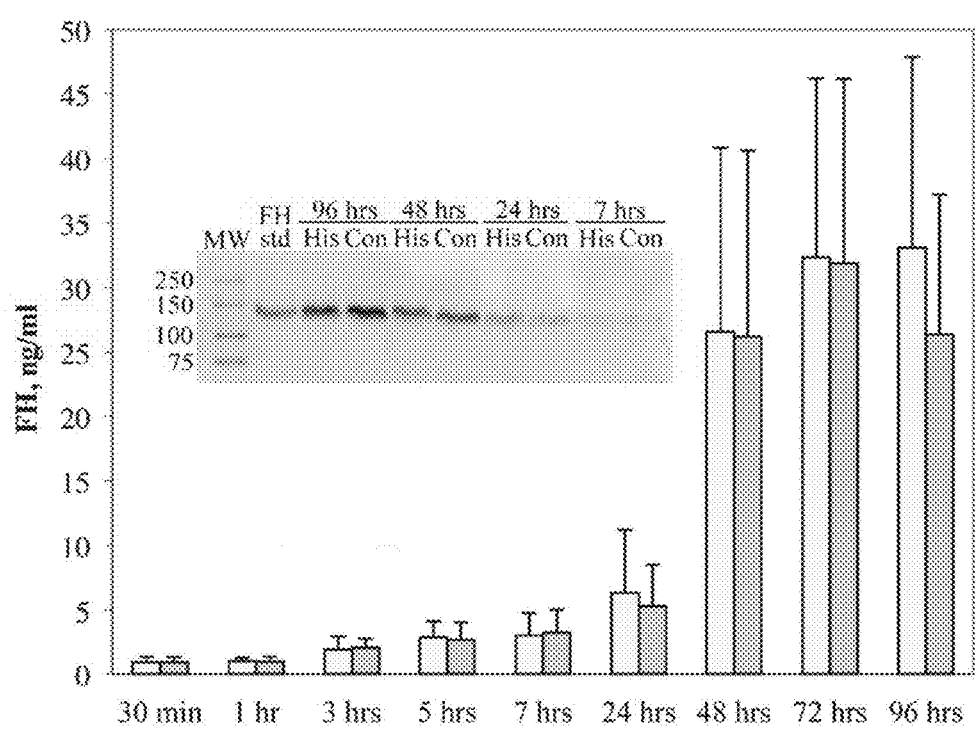

FIG. 1C shows that HUVEC release of FH is unaffected by histamine. Conditioned media was collected from HUVECs in serum-free media (white bars) or serum-free media containing 100 μM histamine (gray bars) at the indicated times. Concentrations of released FH (ng/ml) were measured by fluorescent immunoassay. Means plus standard deviations (n=6) are shown. Inset shows FH detected in HUVEC conditioned media from unstimulated control cells (Con) or histamine-stimulated cells (His) by 7.5% PAGE and Western blotting. MW denotes molecular weight markers in kDa, and FH standard (std) lane contains 31 ng of purified FH protein.

Figure 2A:
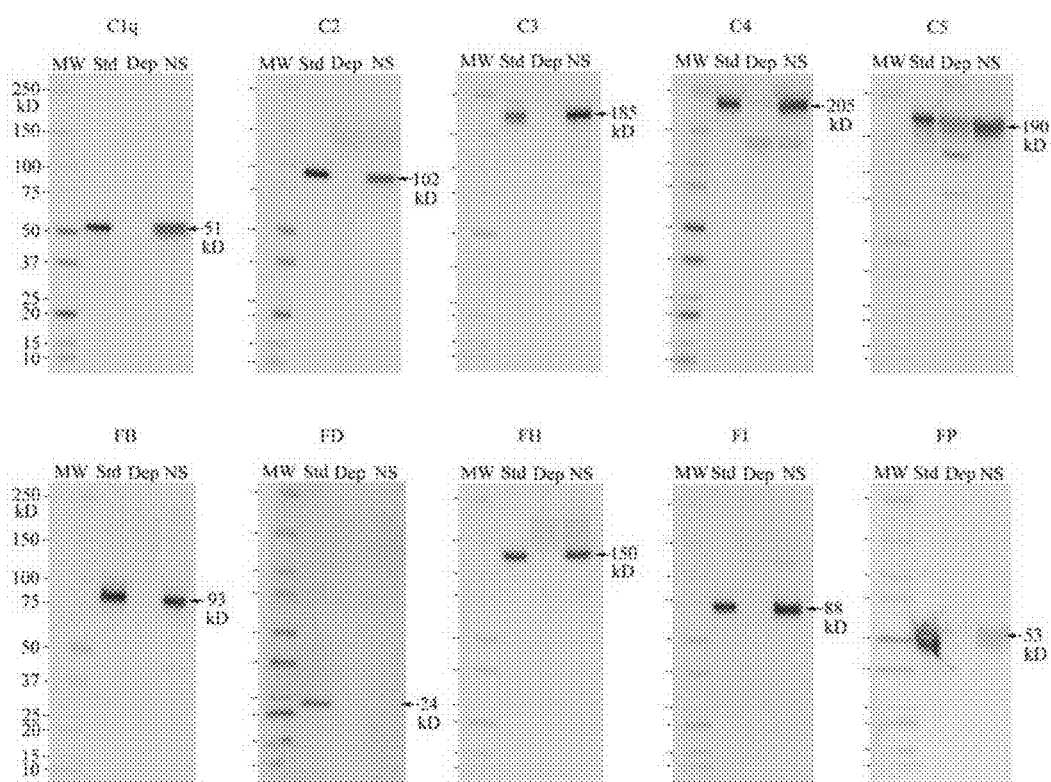

FIG. 2A shows denatured, non-reduced samples were separated by 4-15% SDS-PAGE and transferred blots were detected with polyclonal goat antibodies to single human complement components. Each blot contains lanes with: 50 ng of a purified complement protein (Std); normal serum (NS) containing 50 ng of the specific complement component; and an equal volume of specific complement component-depleted serum (Dep). Arrows show relative molecular mass of protein migration in SDS and MW indicates molecular weight markers in kDa. Quantitative exceptions are detailed in the Methods section.

Figure 2B:
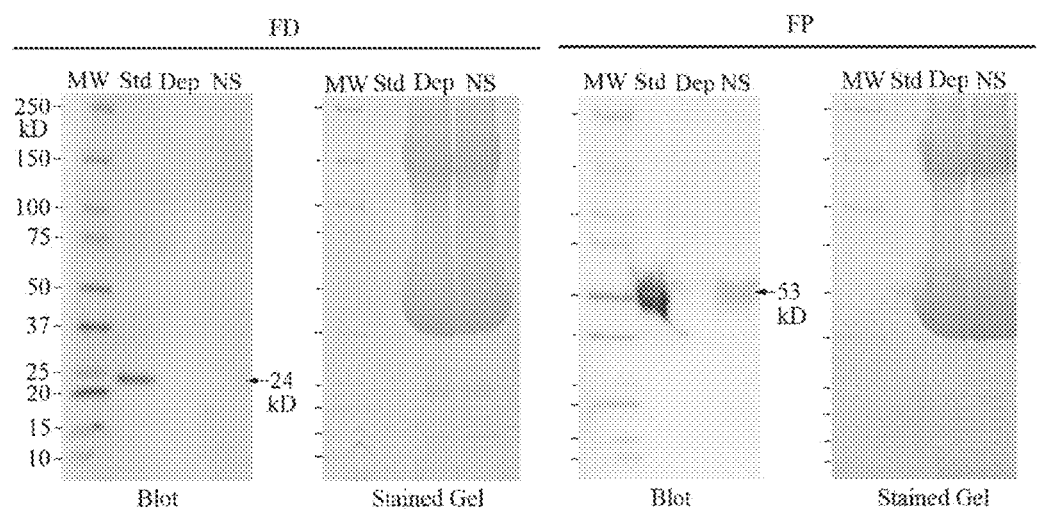

FIG. 2B shows that FD and FP were analyzed by Western blots as described in FIG. 2A except for the following changes: in the FD blot the Std lane contains 159 ng FD and NS lane contains 4 ng FD (FD serum conc. 1-2 ng/μl); and in the FP blot the NS lane contains 10 ng FP (FP serum conc. 4-6 ng/μl). The Coomassie stained gels show the high levels of protein (~100 μg/lane) in the serum samples that were applied to the gels.

Figure 3:
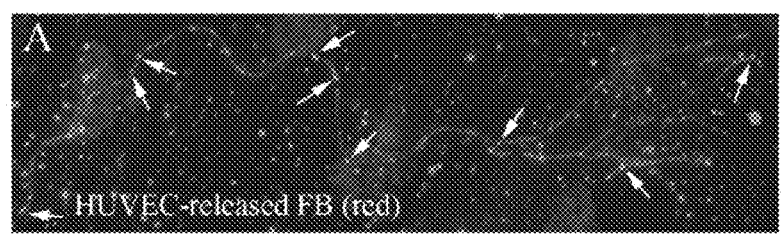
Figure 3:
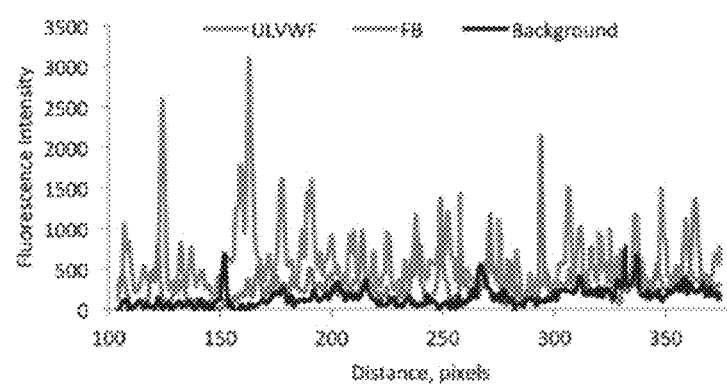
Figure 3:
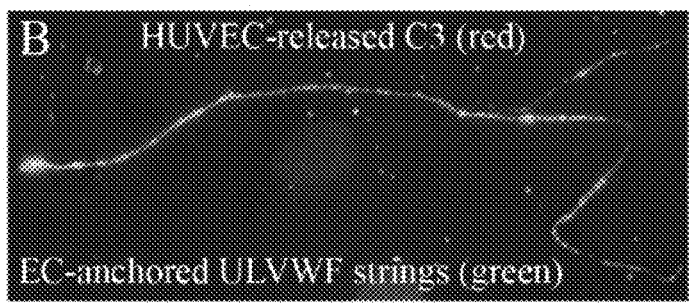
Figure 3:
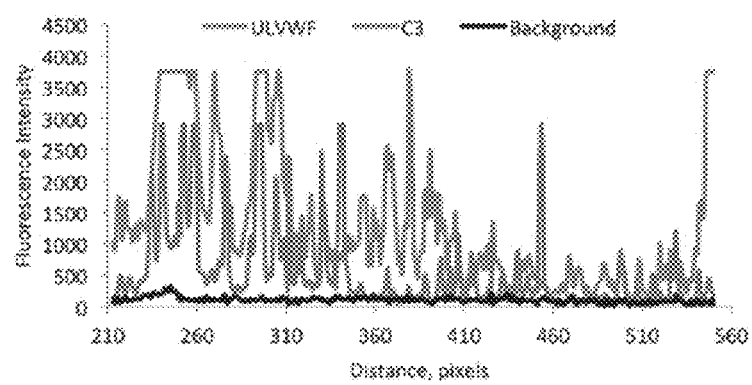
Figure 3:
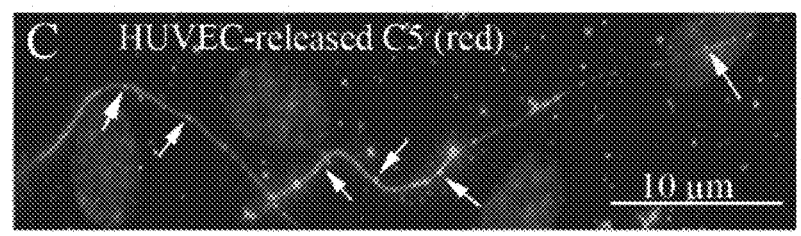
Figure 3:
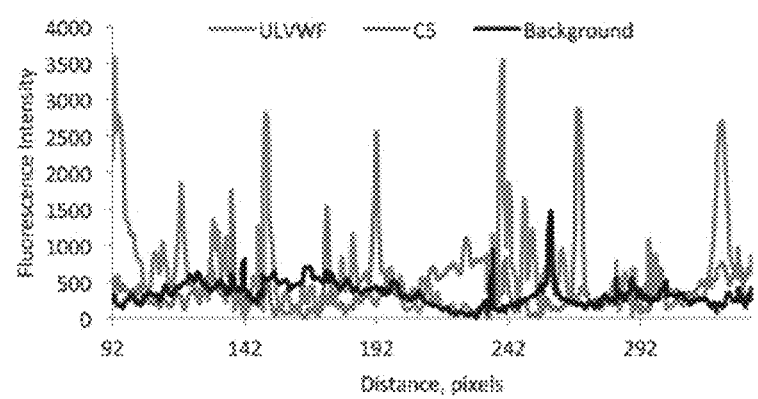
Figure 3:
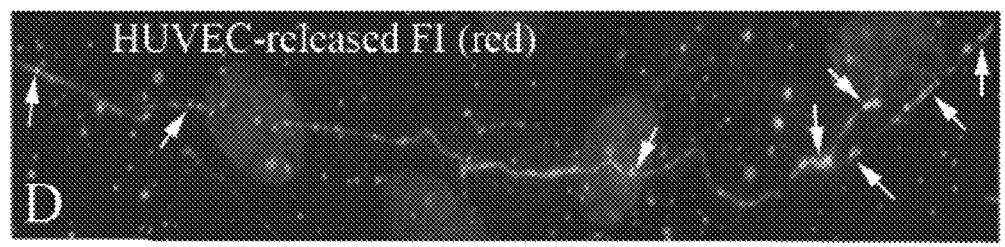
Figure 3:
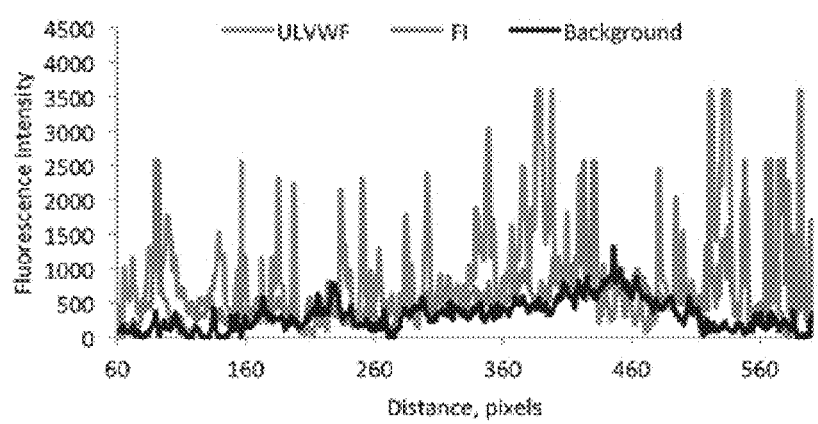
Figure 3:
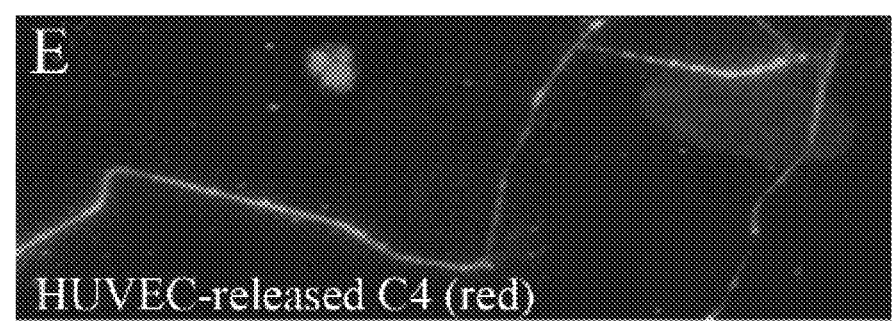
Figure 3:
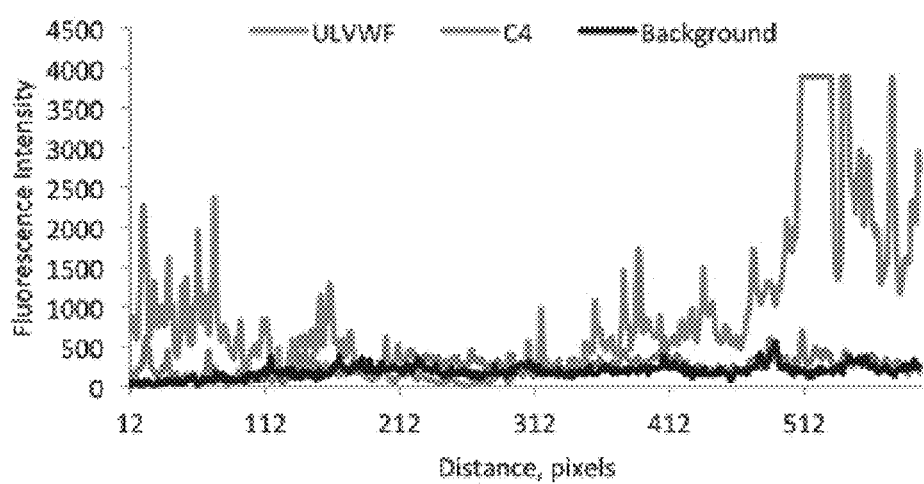

FIG. 3 shows HUVEC-released complement components attach to HUVEC-secreted/anchored ULVWF strings. HUVECs were stimulated with 100 μM histamine and stained with rabbit anti-VWF plus secondary fluorescent anti-rabbit IgG-488 (green). Cells were p-formaldehyde fixed and stained with goat IgG antibodies to human (A) FB, (B) C3, (C) C5, (D) FI or (E) C4 plus secondary fluorescent anti-goat IgG-594 (red). The EC nuclei were labeled with DAPI (blue). Left panels: Fluorescent merged images at 600×. Arrows indicate sites on ULVWF strings with attached antibodies to complement proteins (where necessary for clarity). Right panels: Graphs of fluorescent intensities of antibodies against complement proteins along ULVWF strings. Fluorescent intensities from identical locations in ULVWF string images (488-nm, green) and images of antibodies against complement components proteins (594-nm, red) are plotted against distance (in pixels) along lines generated from tracing ULVWF strings in the 488-nm (green) images. The background intensities of the antibodies against complement components were measured in the 594-nm (red) images at locations away from the areas of interest.

Figure 4:
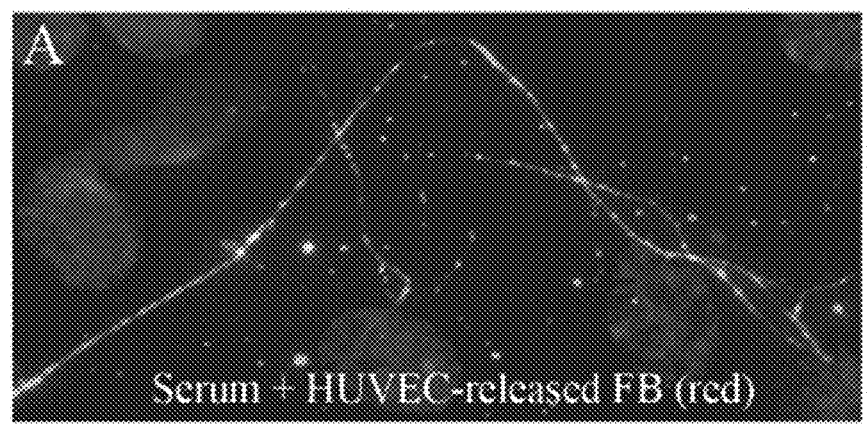
Figure 4:
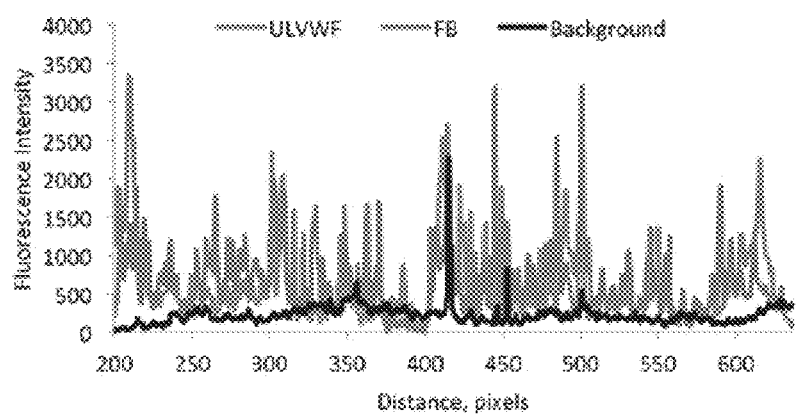
Figure 4:
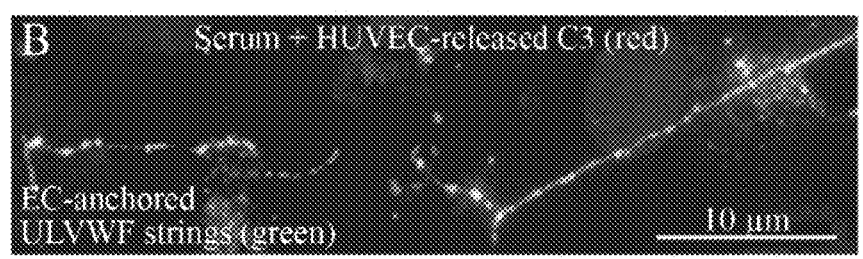
Figure 4:
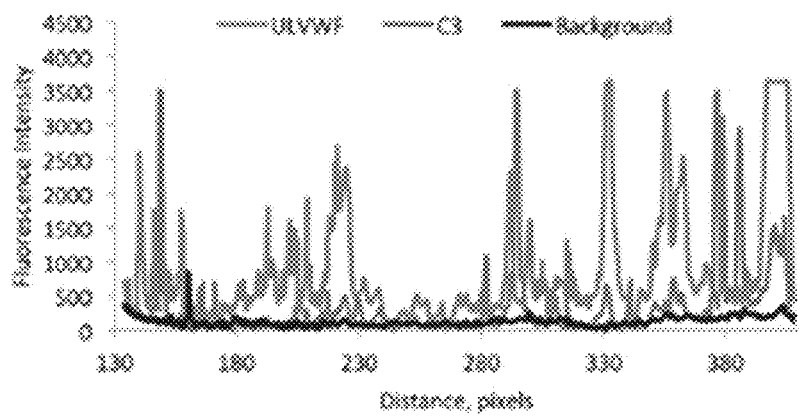
Figure 4:
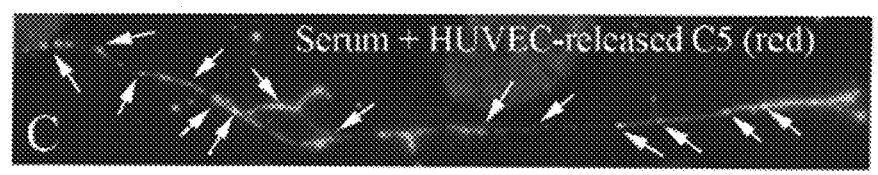
Figure 4:
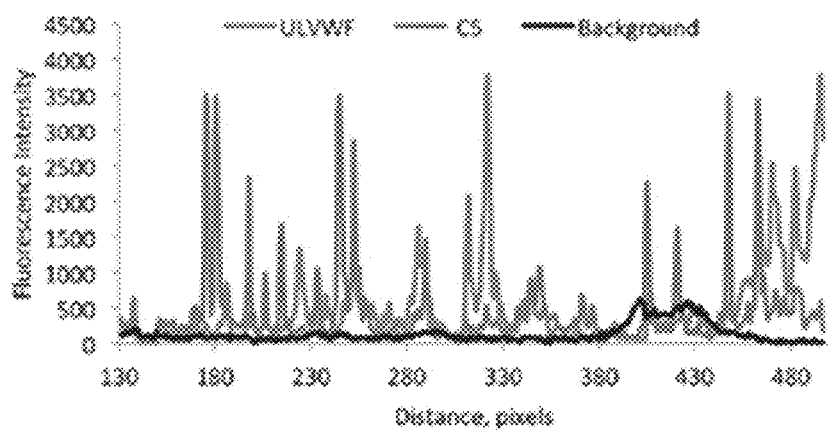
Figure 4:
Figure 4:
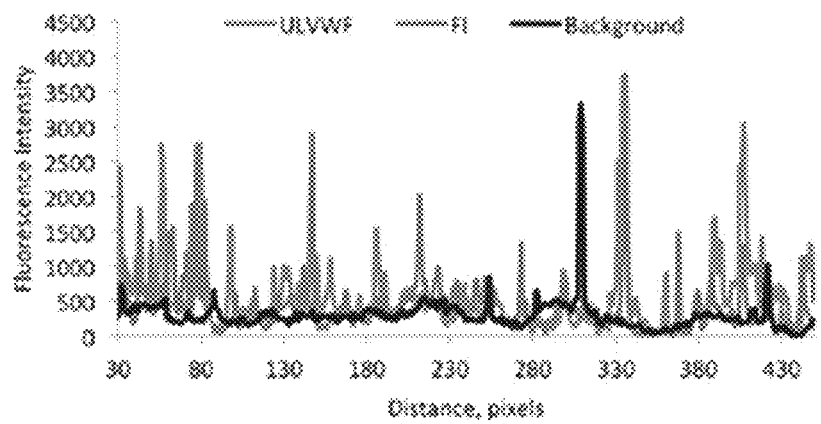
Figure 4:
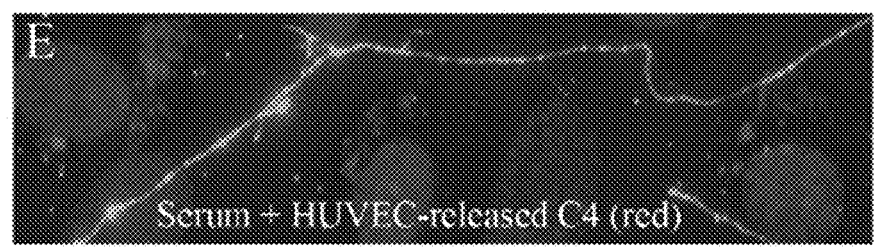
Figure 4:
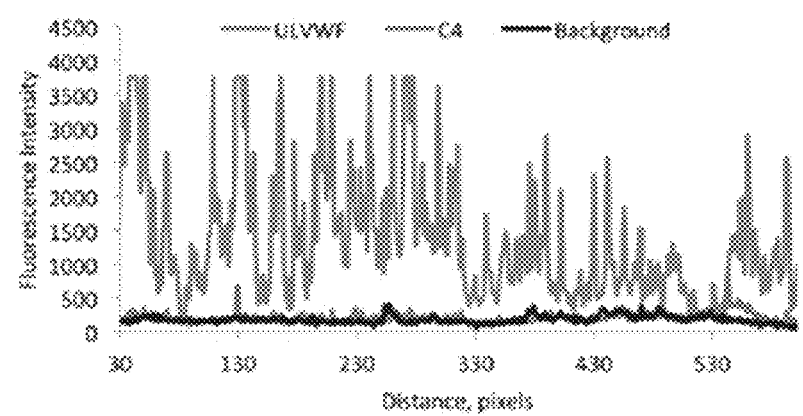

FIG. 4 shows attachment of complement components from heated normal serum to HUVEC secreted/anchored ULVWF strings. HUVECs were stimulated with 100 μM histamine in 25% heated serum/PBS for 5 min, followed by 4 washes of PBS before staining with rabbit anti-VWF plus anti-rabbit IgG-488 (green) and goat antibodies to human (A) FB, (B) C3, (C) C5, (D) FI or (E) C4 plus anti-goat IgG-594 (red) and DAPI. Left panels: Fluorescent merged images at 600×. Arrows indicate sites on ULVWF strings with attached complement antibodies (where necessary for clarity). Right panels: Graphs of fluorescent intensities of antibodies against complement components along ULVWF strings. Details are in the legend for FIG. 3.

Figure 5:
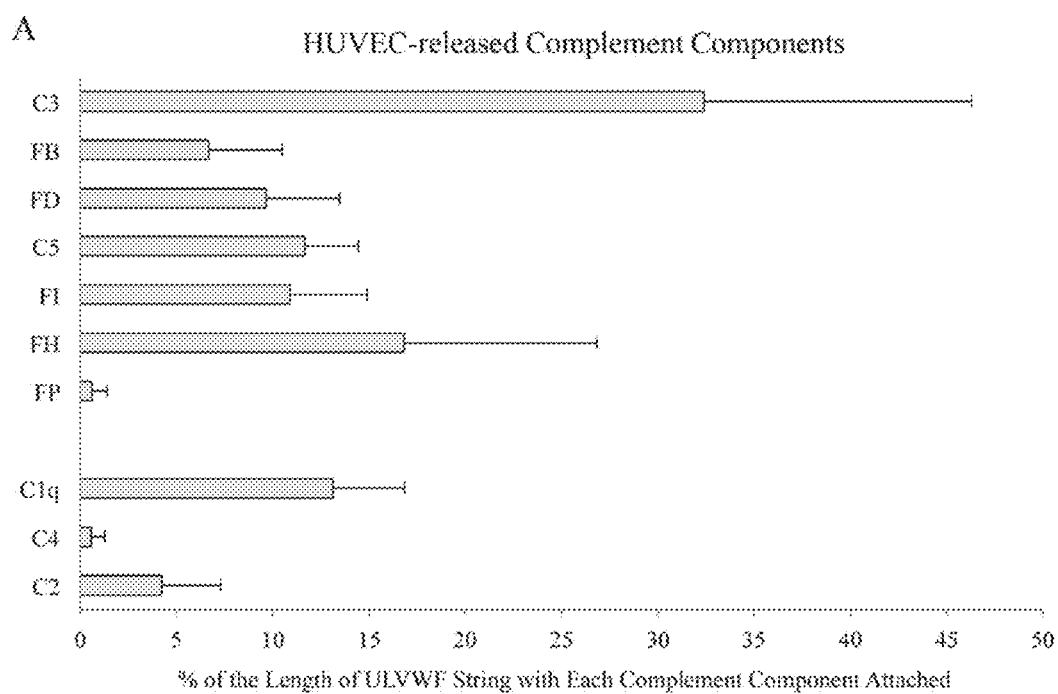
Figure 5:
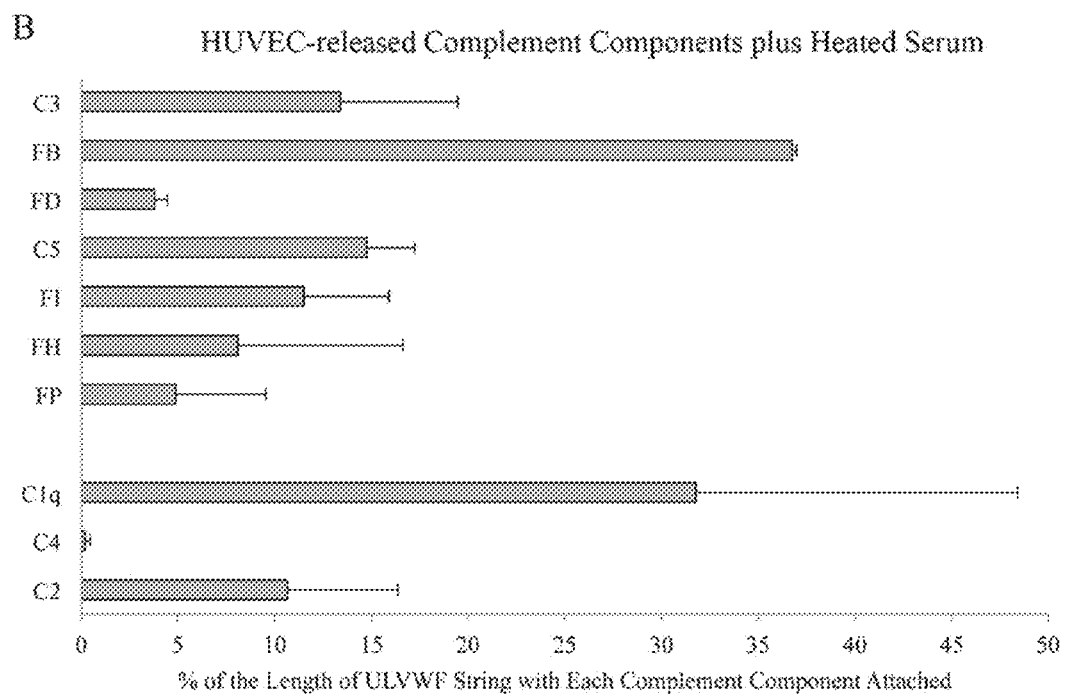

FIG. 5 shows percentage of HUVEC-secreted/anchored ULVWF string lengths with bound complement components: (A) released exclusively from histamine-stimulated HUVECs; or (B) released from stimulated HUVECs plus added in heated normal serum. Shown are the percentages of complement protein intensities (as determined in FIGS. 3 and 4) that were >500 fluorescent units above background per length (in pixels) of ULVWF strings. Values are means plus standard deviations from 3-7 experiments for each complement component.

Figure 6:
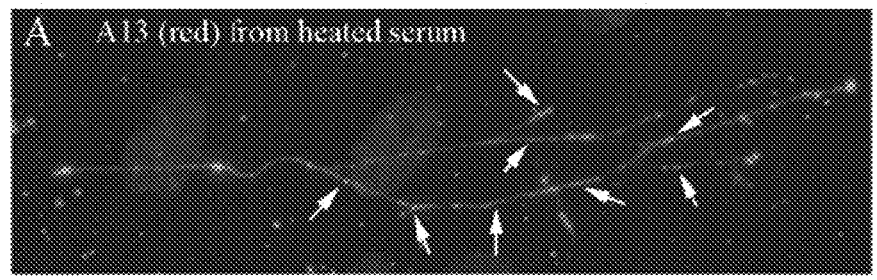
Figure 6:
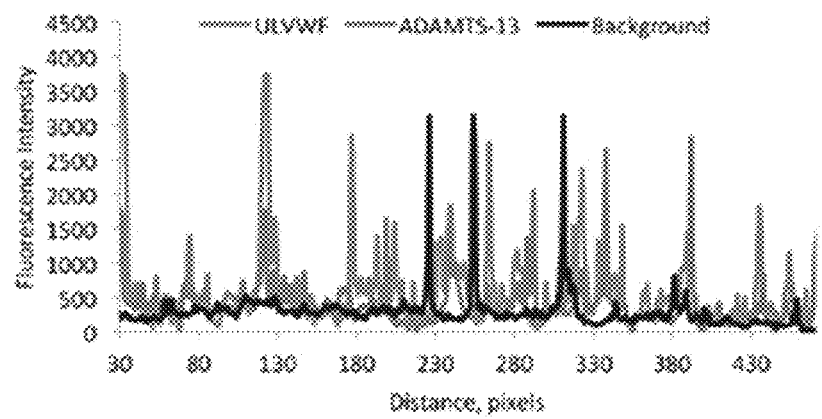
Figure 6:
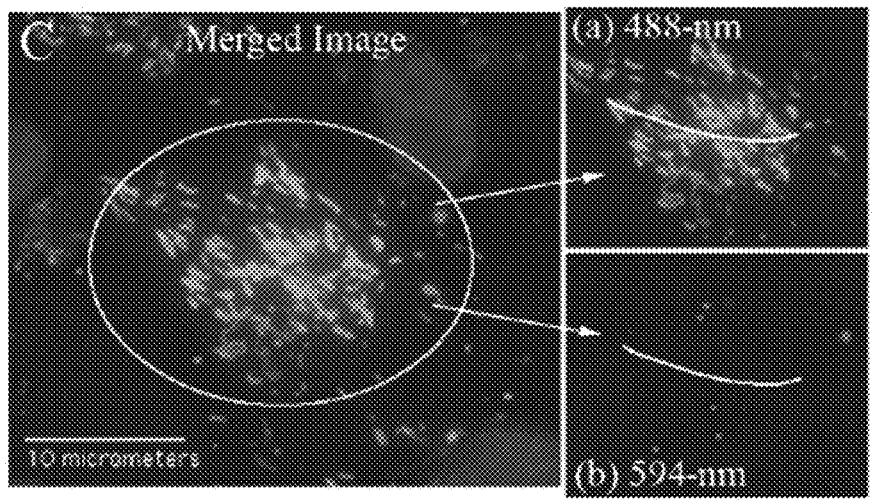
Figure 6:
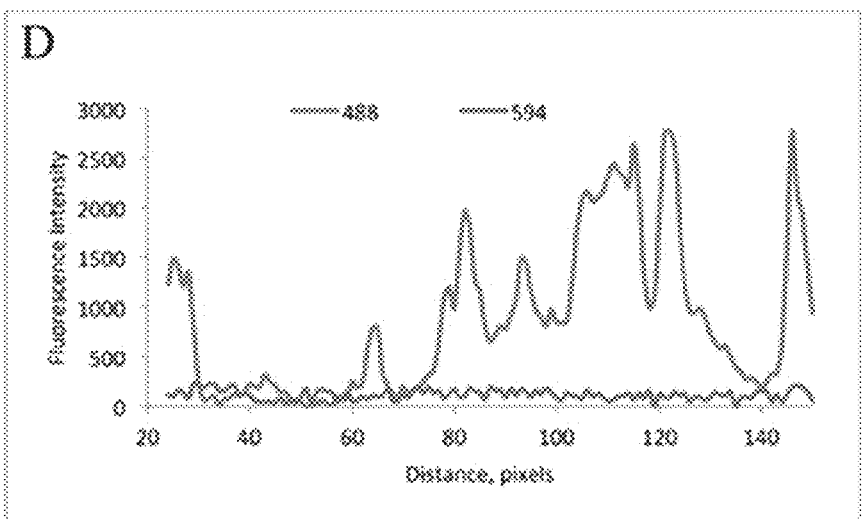
Figure 6:
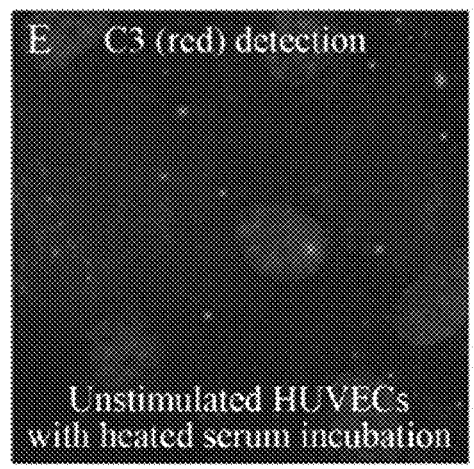
Figure 6:
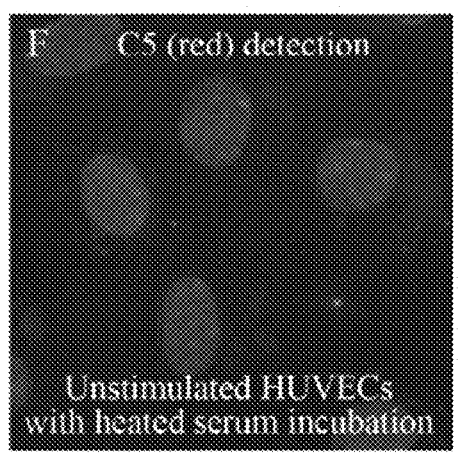

FIG. 6 shows fluorescent microscopy controls. (A-B) Heat denatured ADAMTS-13 attachment to ULVWF strings: HUVECs were stimulated with 100 μM histamine in 25% heated serum/PBS for 5 min, followed by 4 washes of PBS before staining with rabbit anti-VWF plus anti-rabbit IgG-488 (green) and goat anti-ADAMTS-13 plus anti-goat IgG-594 (red). ADAMTS-13 attachment to HUVEC-anchored ULVWF strings was imaged (A) and analyzed (B) as described in FIG. 3. Arrows in (A) indicate attachment of heated, functionally inactive ADAMTS-13 on ULVWF strings (7.5%±2.5). (C-D) Fluorescent emission "bleed-through" controls: Non-stimulated HUVECs were fixed with p-formaldehyde and treated with Triton-X to allow intracellular fluorescent staining VWF in Weibel-Palade bodies was detected with rabbit anti-human VWF plus anti-rabbit IgG-488; and Factor B was detected with goat anti-human FB plus anti-goat IgG-594. (C) The merged image was combined from 488-nm (green) and 594-nm (red) channels at 600× magnification. Single channel emissions of the circled area are shown in the inset images: (a) 488-nm and (b) 594-nm. (D) Graph of fluorescent intensities measured at points along the white lines in inset images (a) and (b) shows that extremely low intensities at 594-nm were measured at the same locations as high intensities were measured in the 488-nm channel, and demonstrates that there was no green-to-red "bleed-through". (E-F) Un-stimulated HUVEC-complement binding controls: Non-stimulated HUVECs were incubated in 25% heated serum/PBS for 5 min, followed by 4 washes of PBS before staining with rabbit anti-VWF plus anti-rabbit IgG-488 (green) and goat antibodies to: (E) C3; or (F) C5; each with anti-goat IgG-594 (red).

Figure 7:
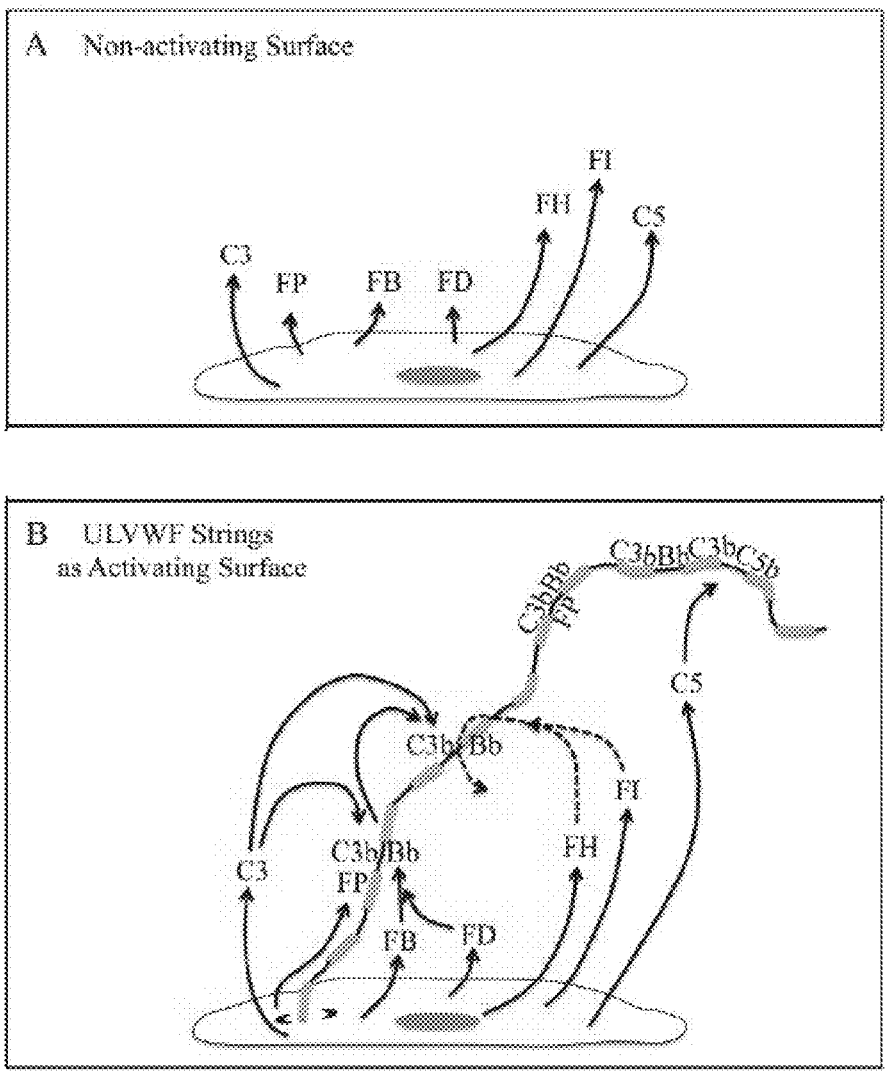
Figure 7:
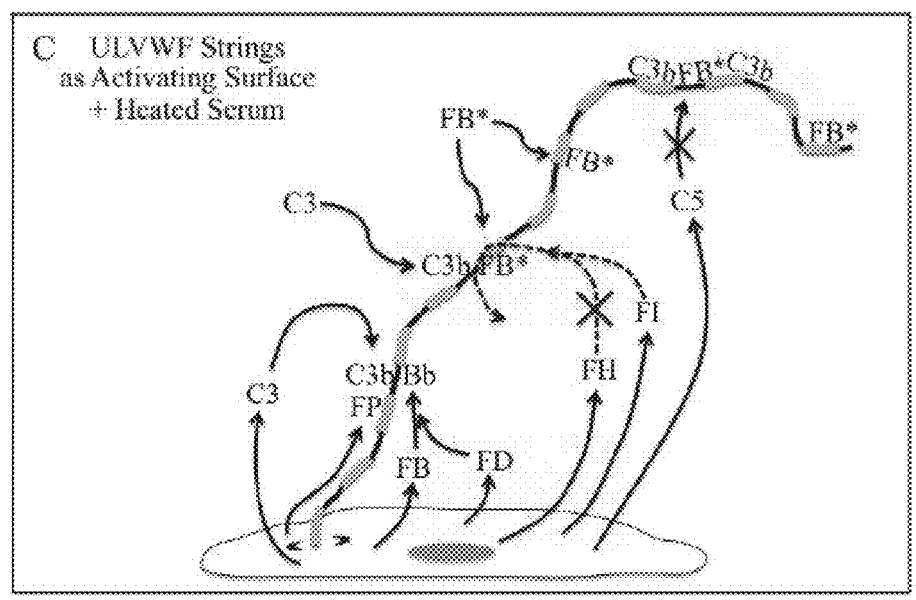

FIG. 7 shows cartoon interpretation of experimental observations. (A) Non-activating surface: In the absence of stimulating agents, HUVEC surfaces were devoid of anchored ULVWF strings. Complement components C3, FP, FB, FD, C5, FH and FI were synthesized and released by HUVECs, but did not attach to the EC surface in the absence of secreted and anchored ULVWF strings. (B) EC-secreted/anchored ULVWF strings as activating surfaces for EC-released complement components: Histamine-secreted, anchored ULVWF strings were covered extensively with C3b. C3 was released, activated and amplified by C3 convertases (C3bBb) assembled on the strings. The C3b attachment to the ULVWF strings allowed C3b-FB attachment and FB cleavage and activation to Bb by FD. The assembled C3 convertase (C3bBb) was stabilized by released FP. As C3b amplification continued, additional C3b molecules attached to ULVWF strings near previously string-assembled C3 convertases to form C5 convertase complexes (C3bBbC3b) capable of inducing C5 binding. The binding of FH to some of the ULVWF string-assembled C3bBb complexes caused displacement of Bb and inactivation of C3b by EC-released FI. (FH and FI are shown by dotted lines.) (C) Addition of heated normal human serum to (B): This resulted in reduced C3b attachment to the histamine-secreted anchored ULVWF strings. Heat-inactivated FB* attached preferentially to ULVWF strings, compared to functional FB released by the HUVECs; however, FB* was not activated to protease form by FD. The binding of inactive FB* to C3b prevented functional C3 convertase formation and, consequently, there was reduced C3b attachment to ULVWF strings compared to exclusively HUVEC-released complement proteins. The reduced C3b attachment prevented C5 convertase assembly and reduced C5 binding to the ULVWF strings. The binding of FH to C3bFB* on ULVWF strings was also reduced when inactivated FB* was a component of C3bFB* complexes (in place of Bb in C3bBb).

Figure 8A:
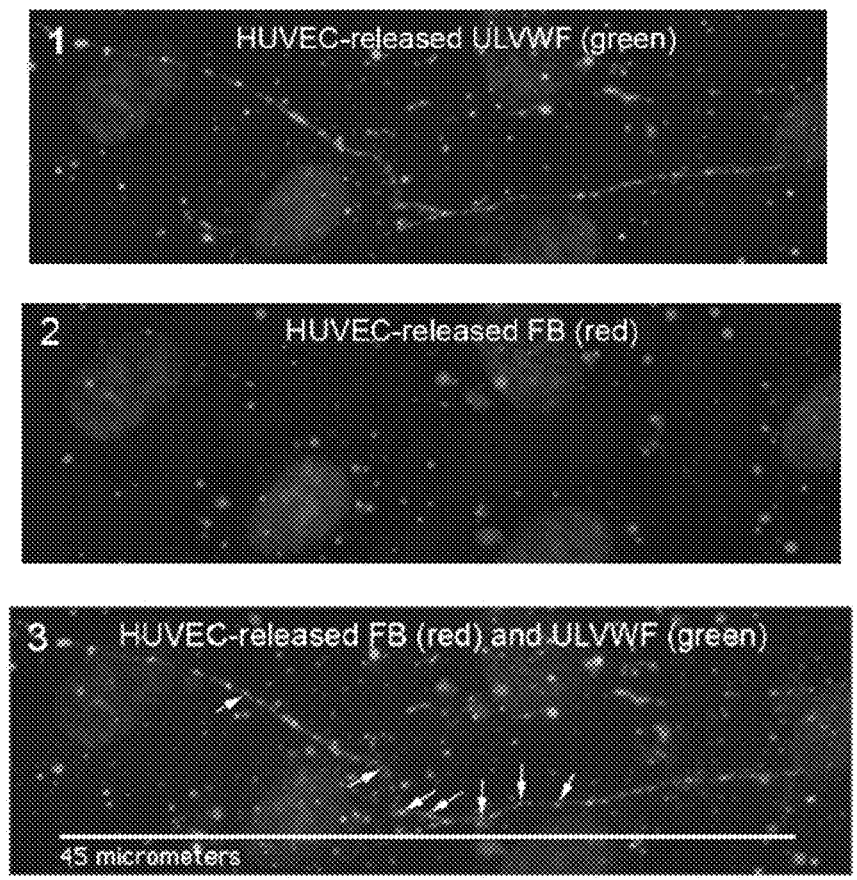
Figure 8A:
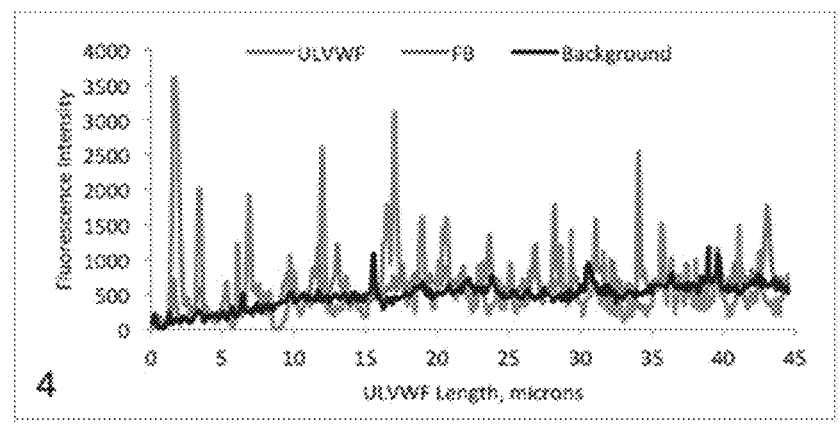
Figure 8A:
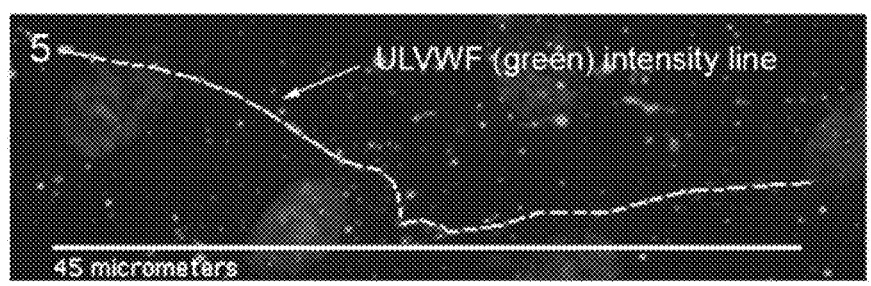
Figure 8A:
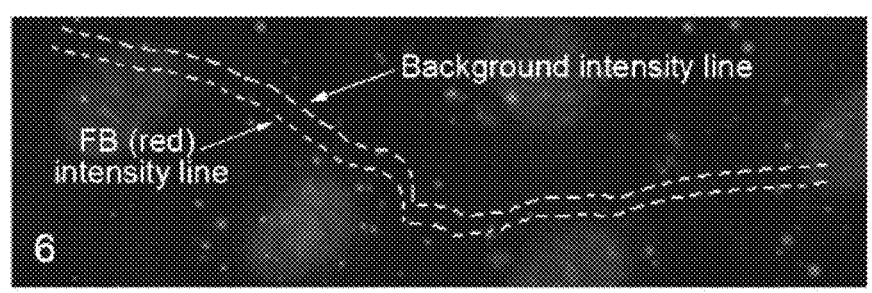

FIG. 8A shows AP-specific component FB attached to ULVWF strings secreted by, and anchored to, stimulated HUVECs. HUVECs were stimulated with 100 μM histamine and stained with rabbit anti-VWF plus secondary fluorescent anti-rabbit IgG-488 (green). Cells were then p-formaldehyde-fixed and stained with goat IgG antibody to human FB. The HUVEC nuclei were labeled with DAPI (blue). (1) ULVWF (488-nm, green); (2) FB (594-nm, red); and (3) ULVWF and FB combined image; (4) Graph of fluorescent intensities (y-axis) measured from identical locations in ULVWF string images (488-nm, green) and in complement component proteins images (594-nm, red) are plotted against the ULVWF string length (in microns, x-axis). The black line indicates the background intensities measured in the 594-nm images. (5) ULVWF intensities were measured along lines of ULVWF strings detected at 488-nm (shown by dotted line); (6) FB intensities were measured in 594-nm images along lines at identical locations (shown by lower dotted line) as determined in (5). Background intensities were also measured in 594-nm (red) images at parallel locations (shown by upper dotted line) away from the area of interest. The white arrows in (3) indicate FB attachment to the strings. Images were selected from 5 independent experiments.

Figure 8B:
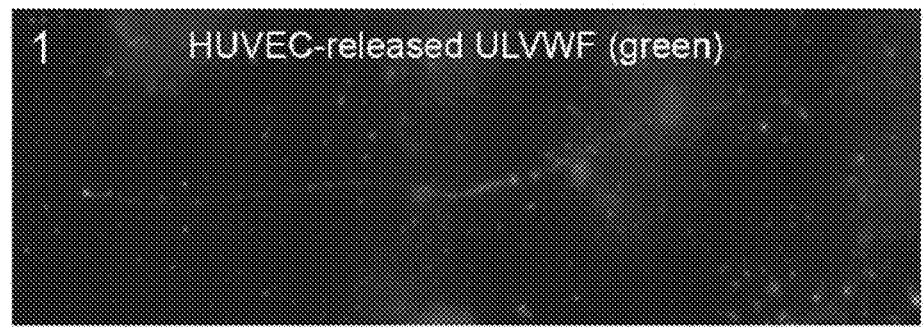
Figure 8B:
Figure 8B:
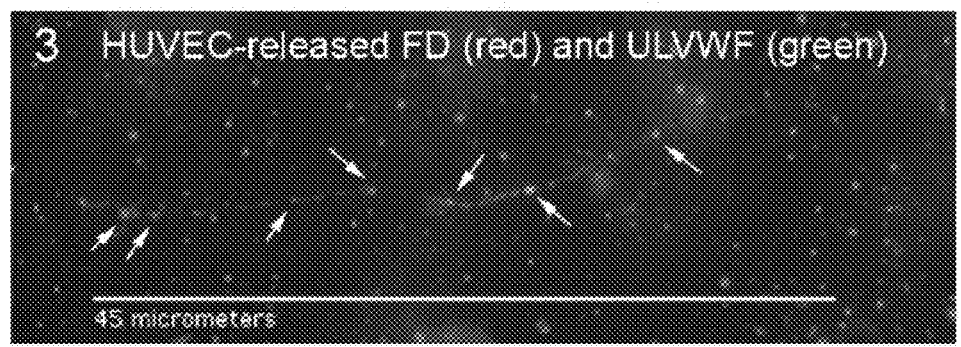
Figure 8B:
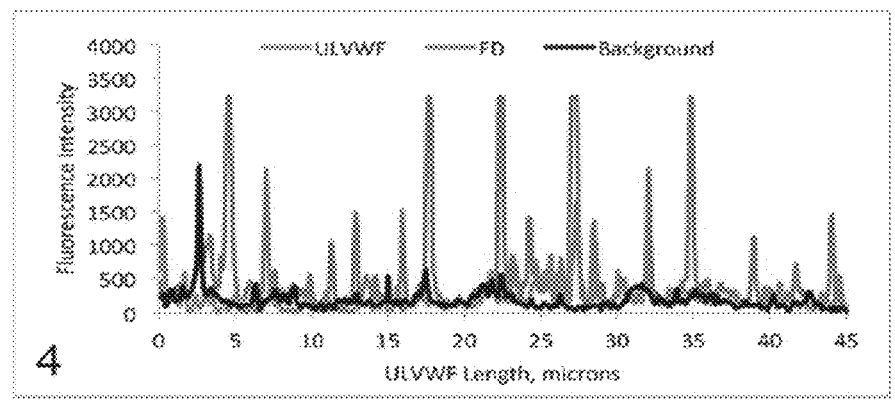
Figure 8B:
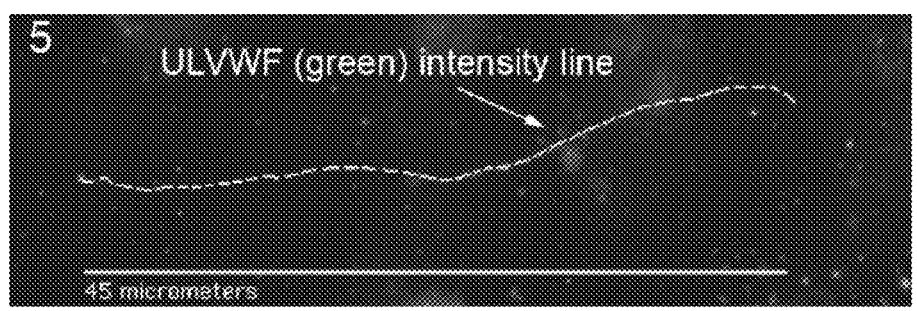
Figure 8B:
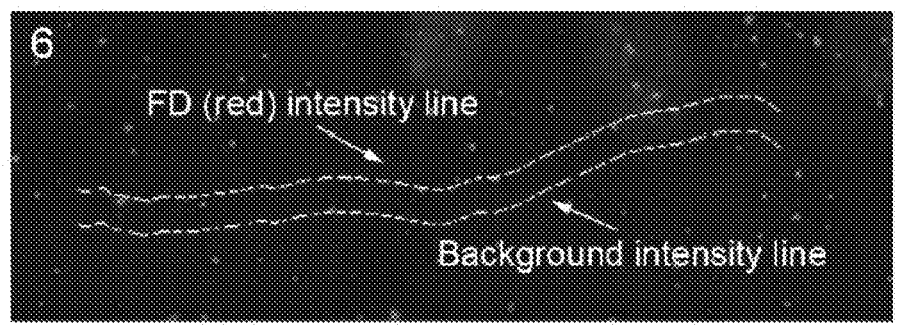

FIG. 8B is similar to the experiment performed in FIG. 8A except that the cells were stained with antibody to human FD to show AP-specific component FD attached to ULVWF strings secreted by, and anchored to, stimulated HUVECs. The white arrows in (3) indicate FD attachment to the strings. Images were selected from 5 independent experiments.

Figure 8C:
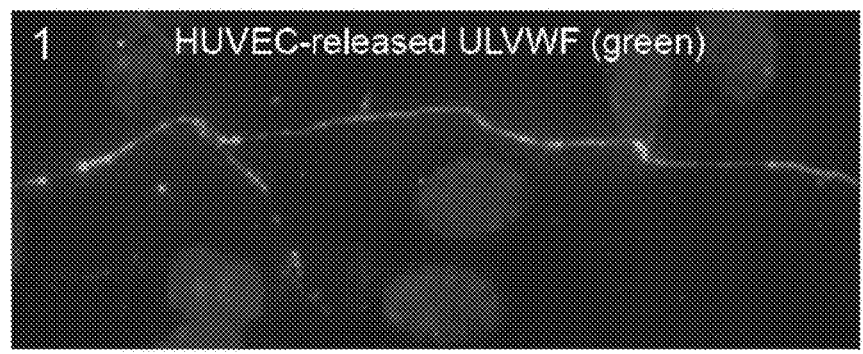
Figure 8C:
Figure 8C:
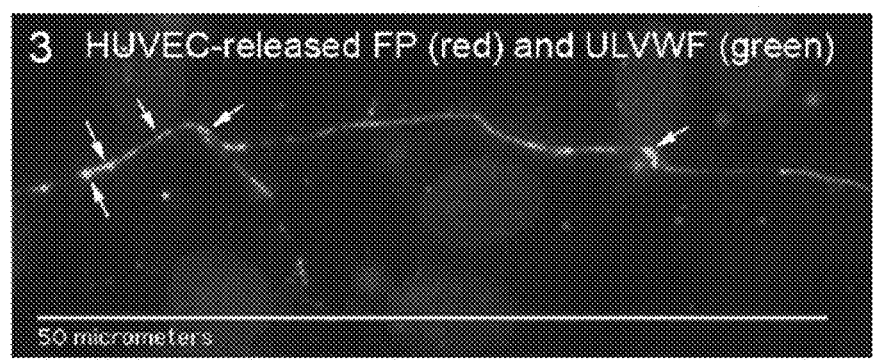
Figure 8C:
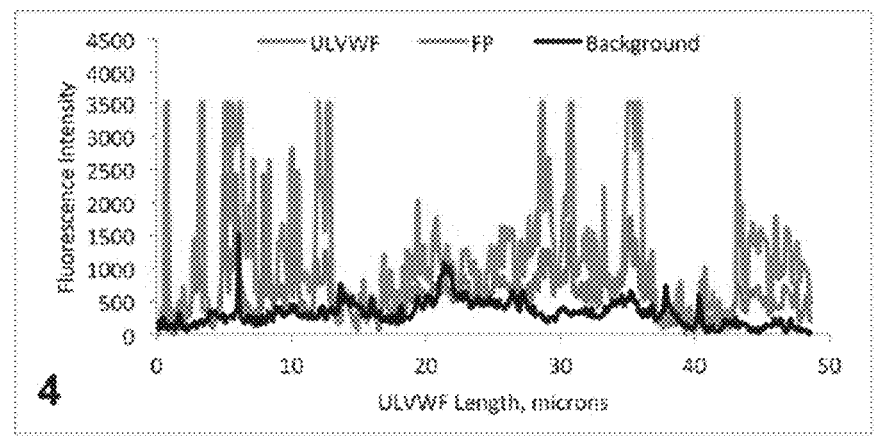
Figure 8C:
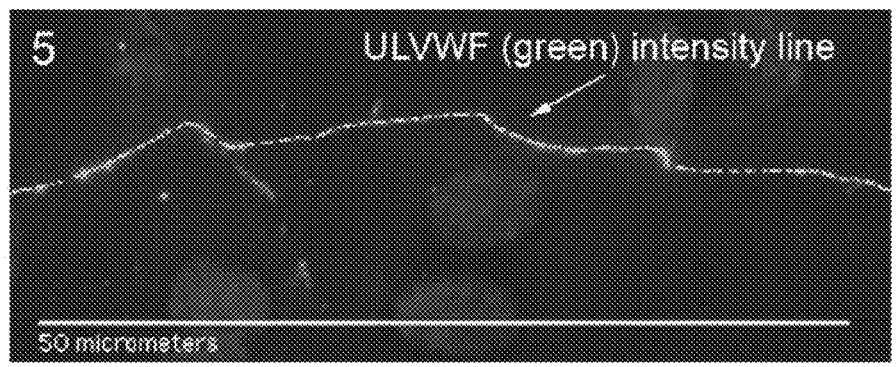
Figure 8C:
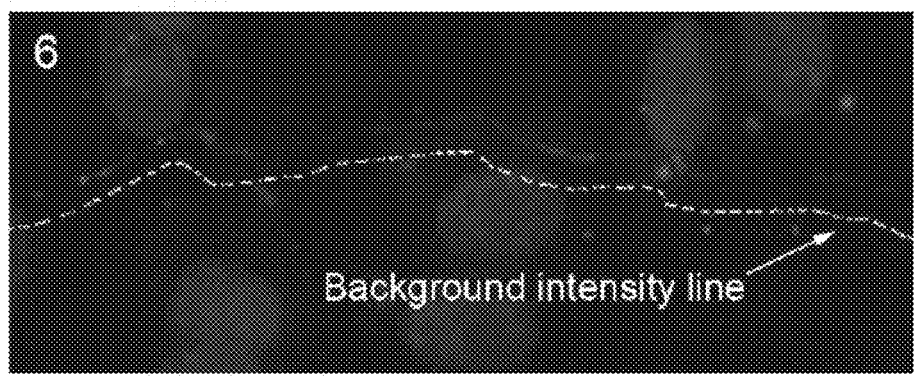

FIG. 8C is similar to the experiment performed in FIG. 8A except that the cells were stained with antibody to human FP to show AP-specific component FP attached to ULVWF strings secreted by, and anchored to, stimulated HUVECs. In panel 6, only the locations of the background intensities are identified by the dotted line. The white arrows in (3) indicate FP attachment to the strings. Images were selected from 4 independent experiments.

Figure 9:
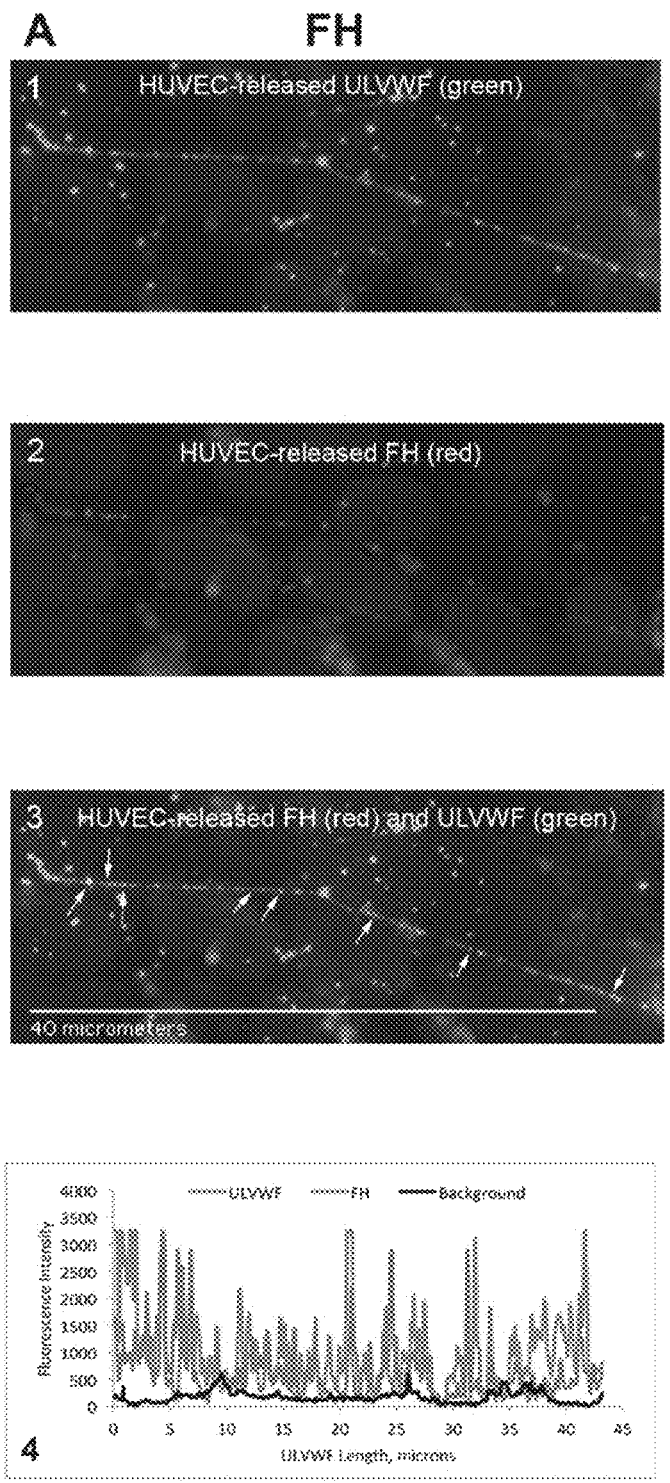
Figure 9:
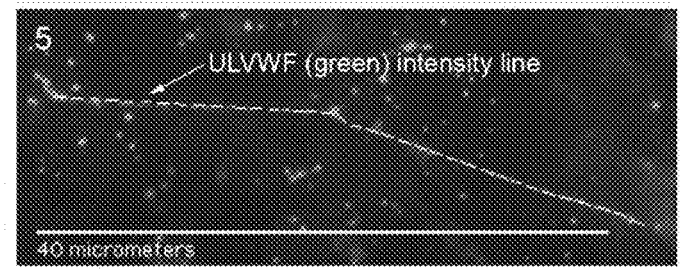
Figure 9:
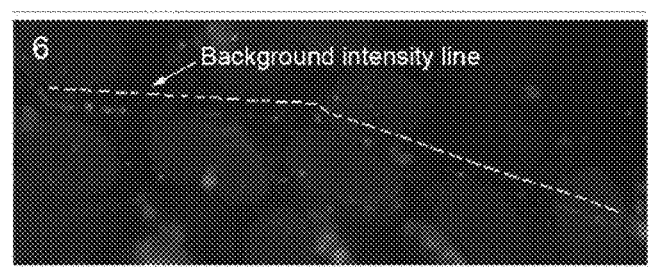
Figure 9:
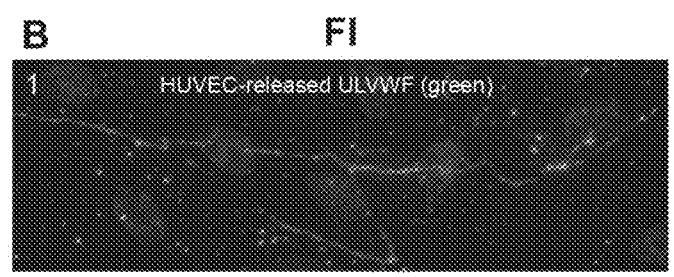
Figure 9:
Figure 9:
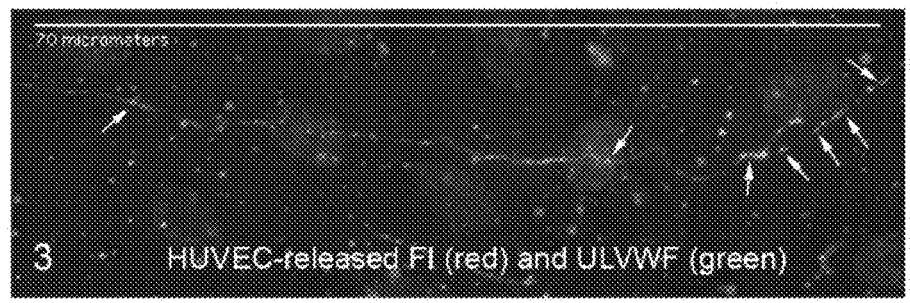
Figure 9:
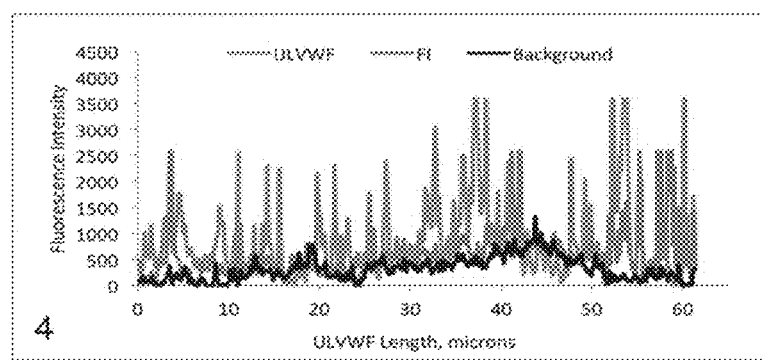
Figure 9:
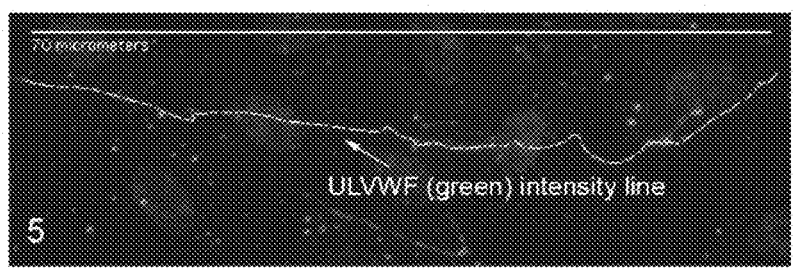
Figure 9:
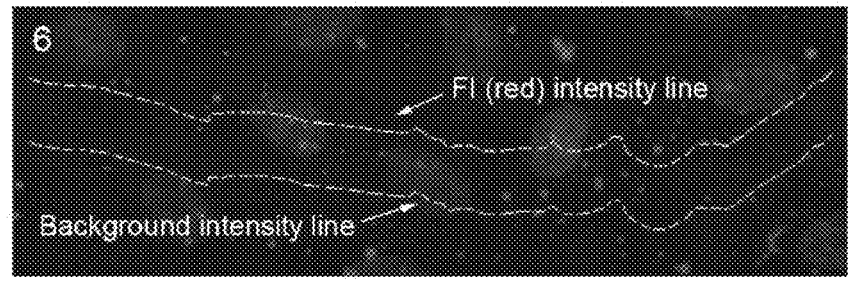

FIG. 9 shows AP-specific negative regulatory components FH and FI attach to ULVWF strings secreted by, and anchored to, stimulated HUVECs. HUVECs were stimulated and stained as in the legend for FIG. 8, except that antibody to human FH was used in (A) and antibody to human FI in (B) to identify complement component attachment to the ULVWF strings. In (A) panel 6, only the locations of the background intensities are identified by the dotted line. In (B) panel 6, the upper dotted line shows the location of the FI intensity measurements and the lower dotted line identifies the locations of background intensity measurements. The white arrows in (3) indicate FH (A) and FI (B) attachment to the strings. Images were selected from 12 (FH) and 4 (FI) independent experiments.

Figure 10:
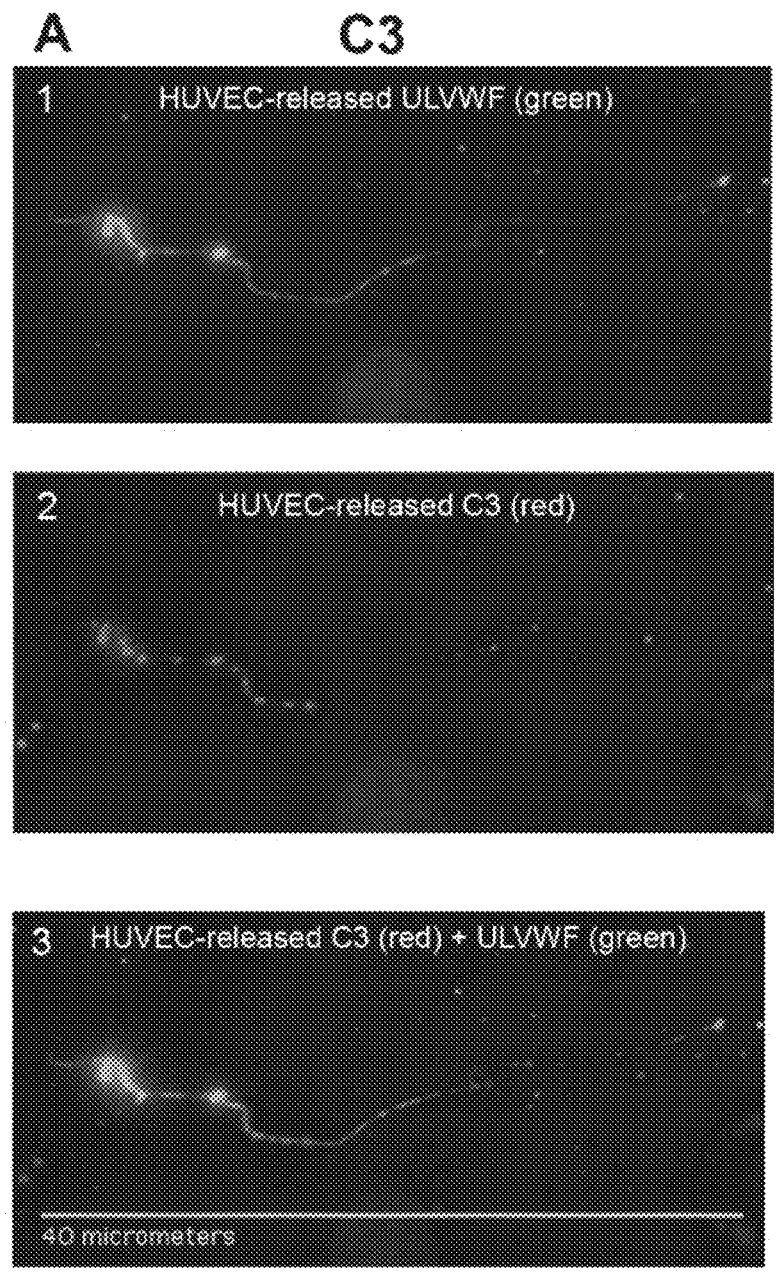
Figure 10:
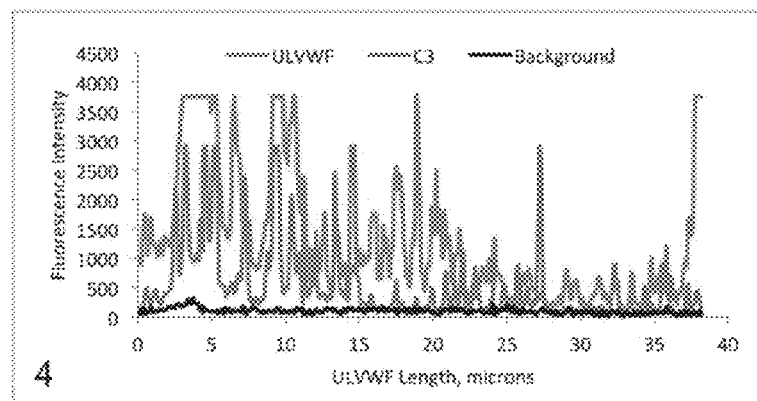
Figure 10:
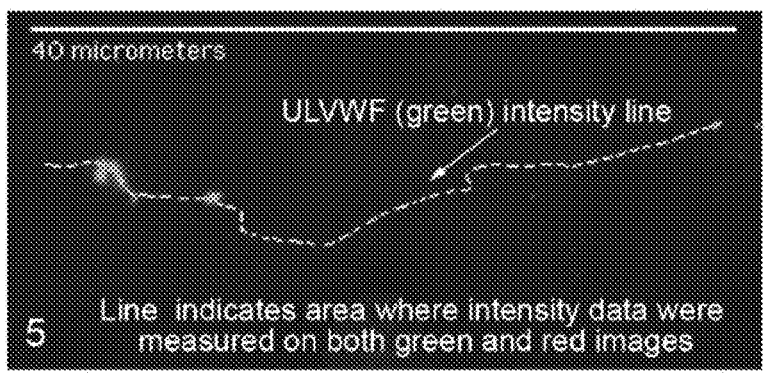
Figure 10:
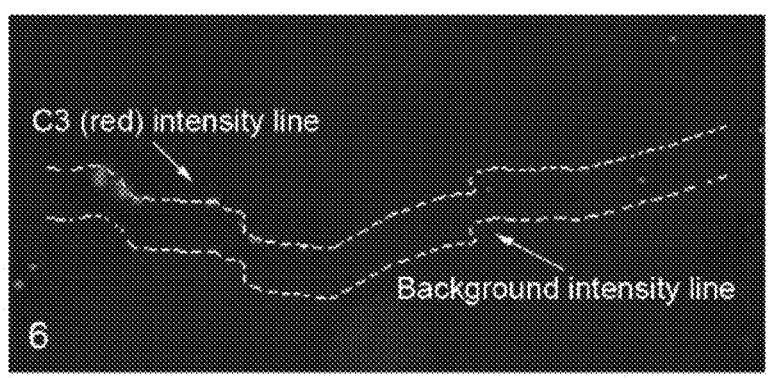
Figure 10:
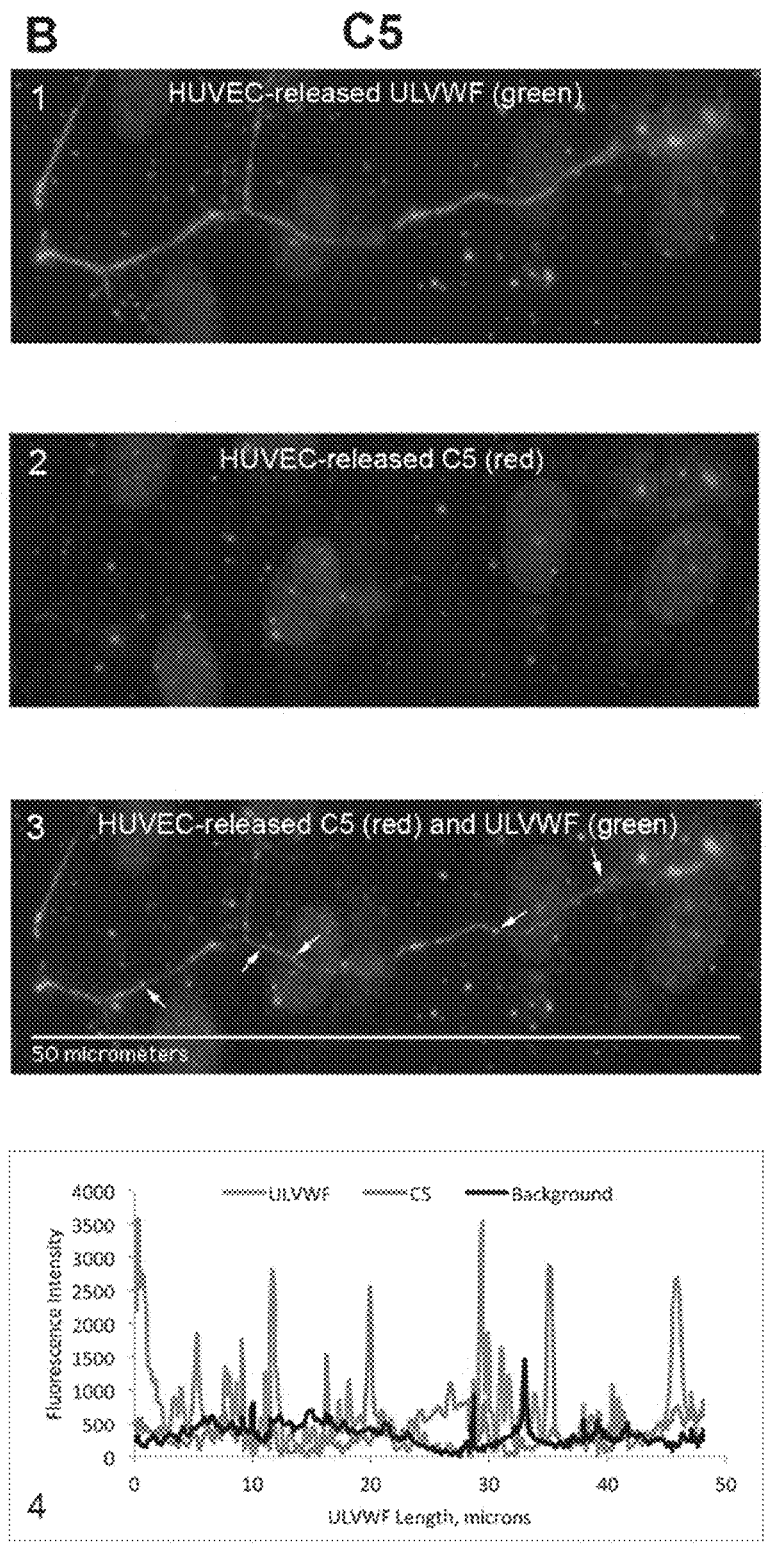
Figure 10:
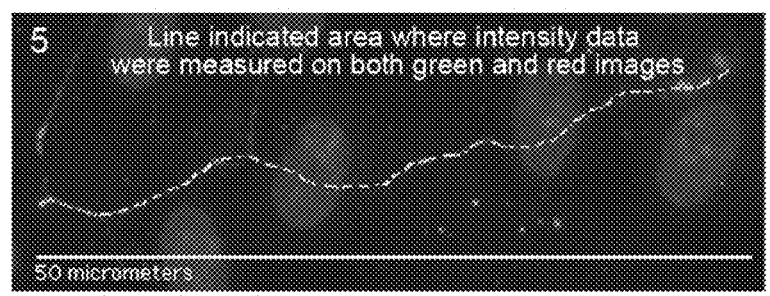
Figure 10:
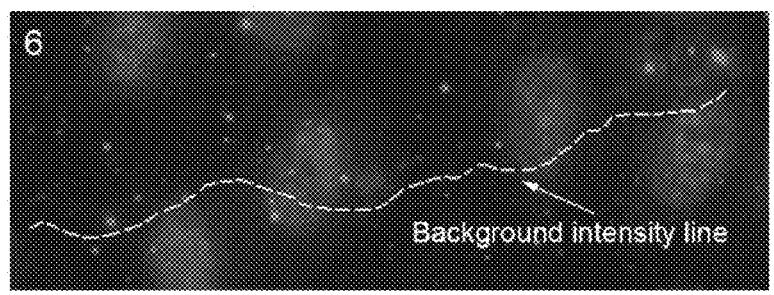

FIG. 10 shows complement components C3 and C5 attach to ULVWF strings secreted by, and anchored to, stimulated HUVECs. HUVECs were stimulated and stained as in the legend for FIG. 8, except that antibody to human C3 was used in (A) and antibody to human C5 in (B) to identify complement component attachment to the ULVWF strings. In (A) panel 6, the upper dotted line shows the location of the C3 intensity measurements and the lower dotted line identifies the locations of background intensity measurements. In (B) panel 6, only the locations of the background intensities are identified by the dotted line. The white arrows in (B) panel 3 indicate C5 attachment to the strings. Images were selected from 6 (C3) and 5 (C5) independent experiments.

Figure 11:
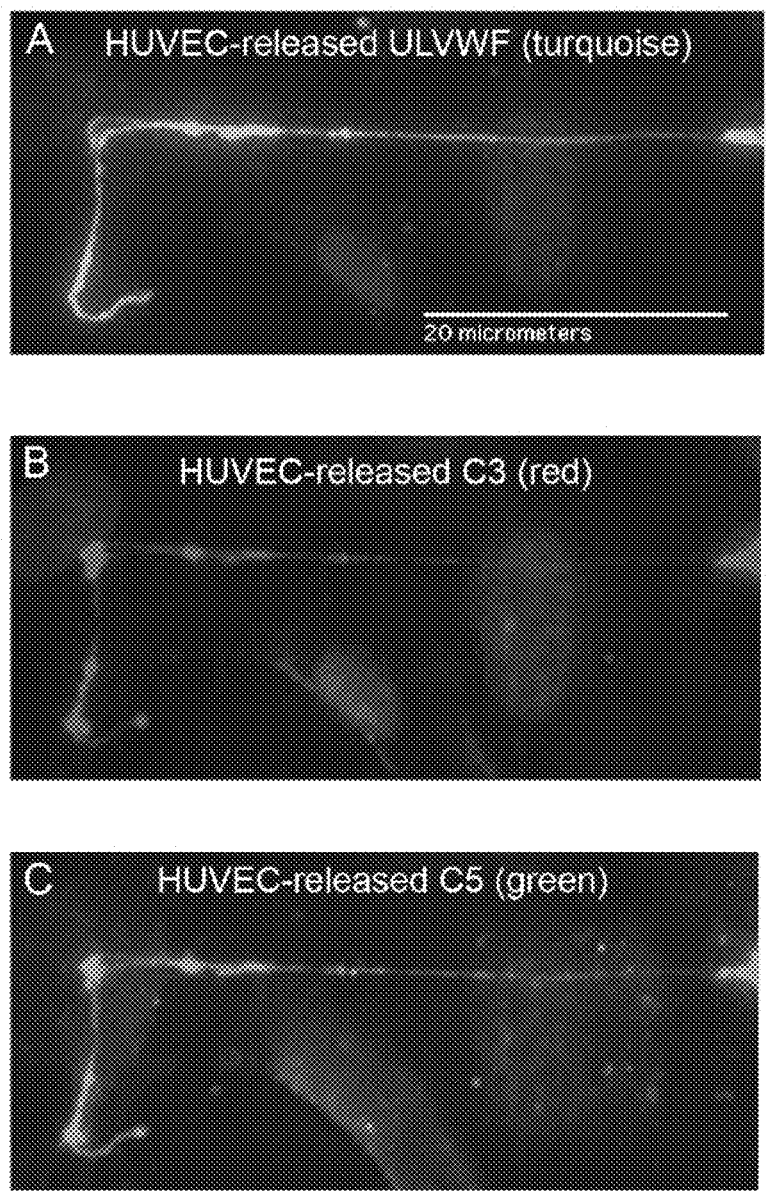
Figure 11:
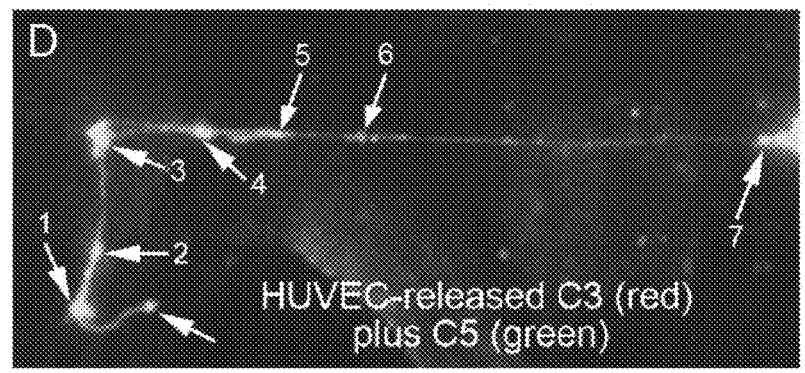
Figure 11:
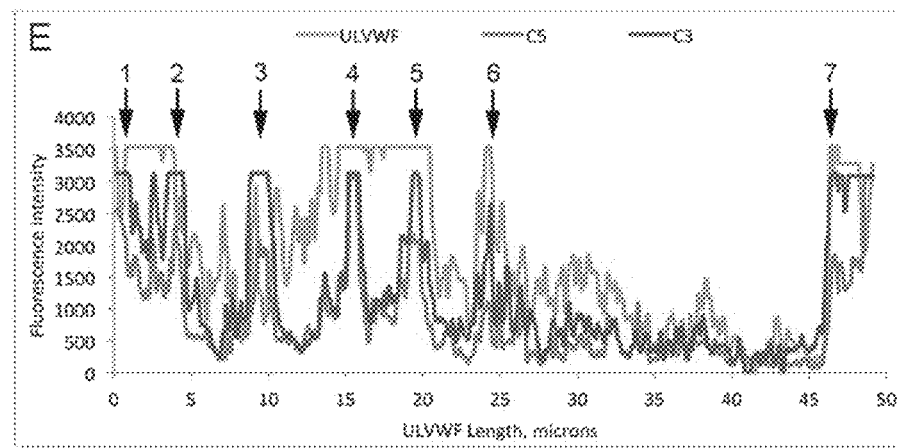

FIG. 11 shows complement components C3 and C5 attach to the same positions along HUVEC secreted/anchored ULVWF strings. HUVECs were stimulated and stained as in the legend for FIG. 8, except that the cells were simultaneously stained for C3 and C5 (in addition to VWF and DAPI). Individual fluorescent channels detected: (A) rabbit anti-VWF plus anti-rabbit IgG-488 (turquoise); (B) a combination of two mouse monoclonal antibodies to human C3 (clone 755 against C3b and clone 10A1 against C3) plus anti-mouse IgG-647 (red); and (C) goat anti-human C5 plus anti-goat IgG-594 (green). (D) Simultaneous detection of C3 (red) and C5 (green) is colored yellow in the combined image from 647- and 594-nm channels. White arrows indicate points along the ULVWF strings where high intensity levels of C3 and C5 were detected. (E) Graph of fluorescent intensities (y-axis) along the ULVWF string (488-nm, turquoise), C3 (647-nm, red) and C5 (594-nm, green) are plotted against the ULVWF string length (in microns, x-axis). The black numbered arrows correspond to the white numbered arrows in (D) and point to the C3 and C5 peak intensity locations. Images were selected from 9 experiments with simultaneous VWF, C3 and C5 staining.

Figure 12:
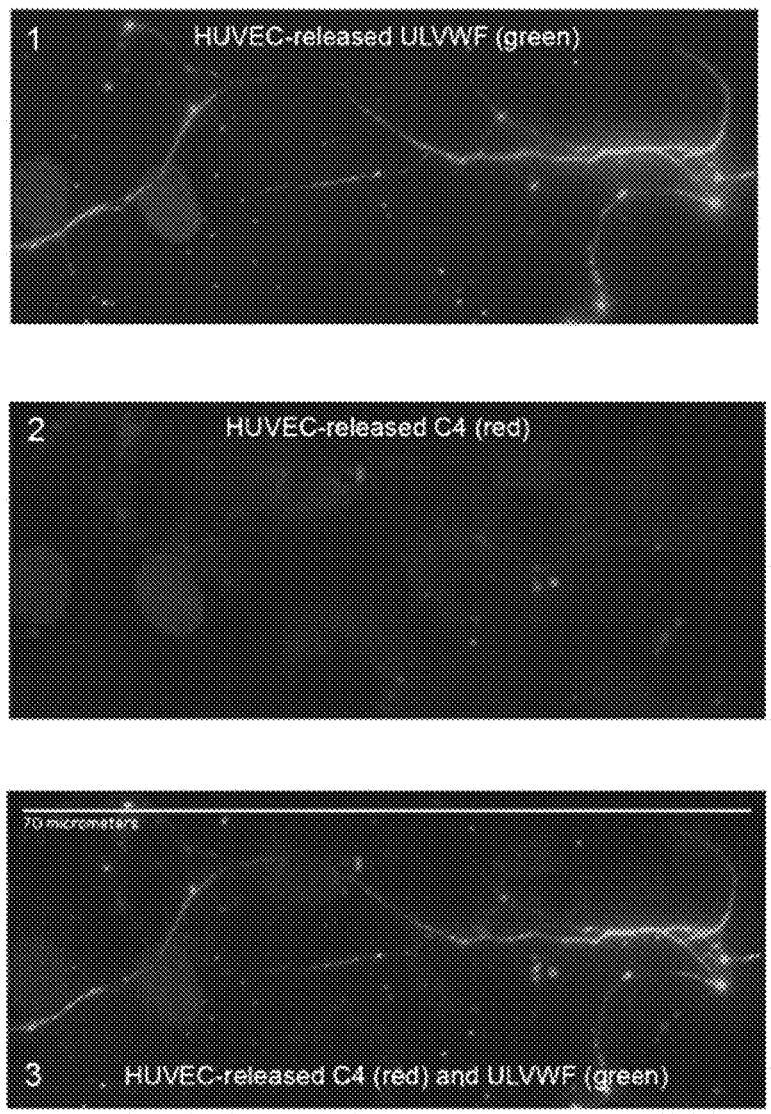
Figure 12:
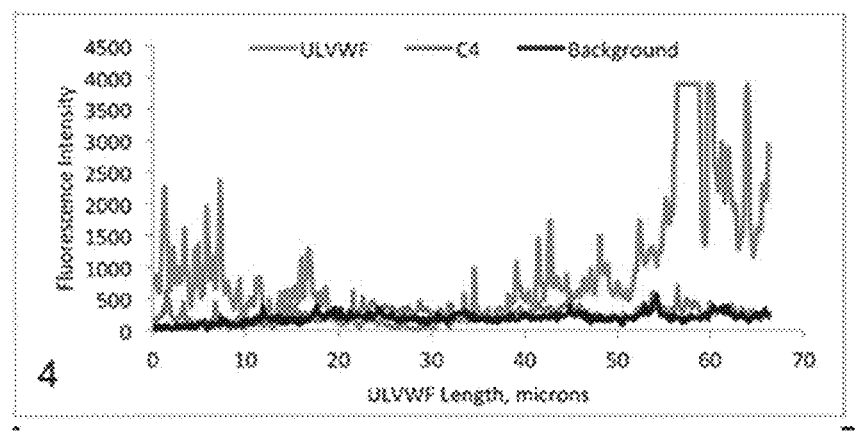
Figure 12:
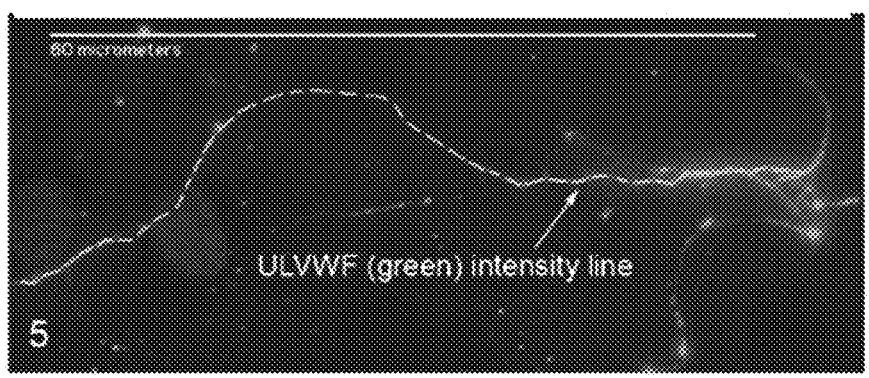
Figure 12:
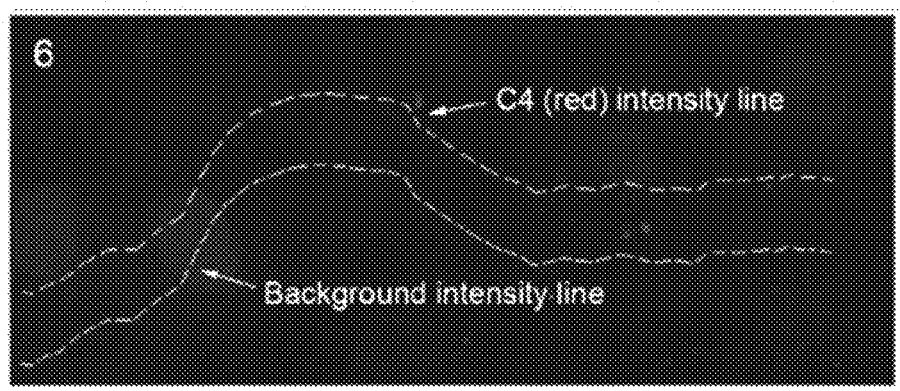

FIG. 12 shows that C4, a component of the classical and lectin pathways, does not attach to ULVWF strings secreted by, and anchored to, stimulated HUVECs. HUVECs were stimulated and stained as in the legend for FIG. 8, except the antibody to human C4 was used to identify complement component attachment to the ULVWF strings. In panel 6, the upper dotted line shows the location of the C4 intensity measurements and the lower dotted line identifies the locations of background intensity measurements. Images were selected from 4 experiments.

Figure 13:
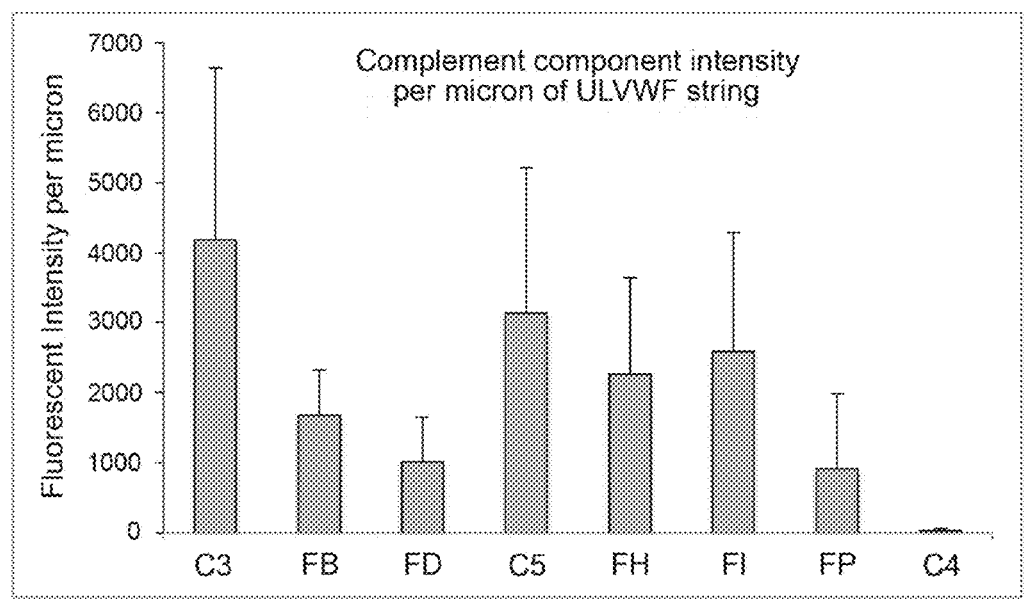

FIG. 13 shows quantification of HUVEC-released complement components attached to HUVEC-secreted/anchored ULVWF strings. Intensities of each HUVEC-released complement proteins were measured along histamine-stimulated HUVEC-secreted/anchored ULVWF strings, as described in the legend for FIG. 8. Shown are the complement component fluorescent intensities per micron of ULVWF string length after background subtraction. Values are means plus SD; N=7-12 strings for each complement component from 4 to 12 experiments and were compiled from 130 fluorescent images. Some data were collected from images within the same experiment at a different location on the coverslip.

Figure 14:
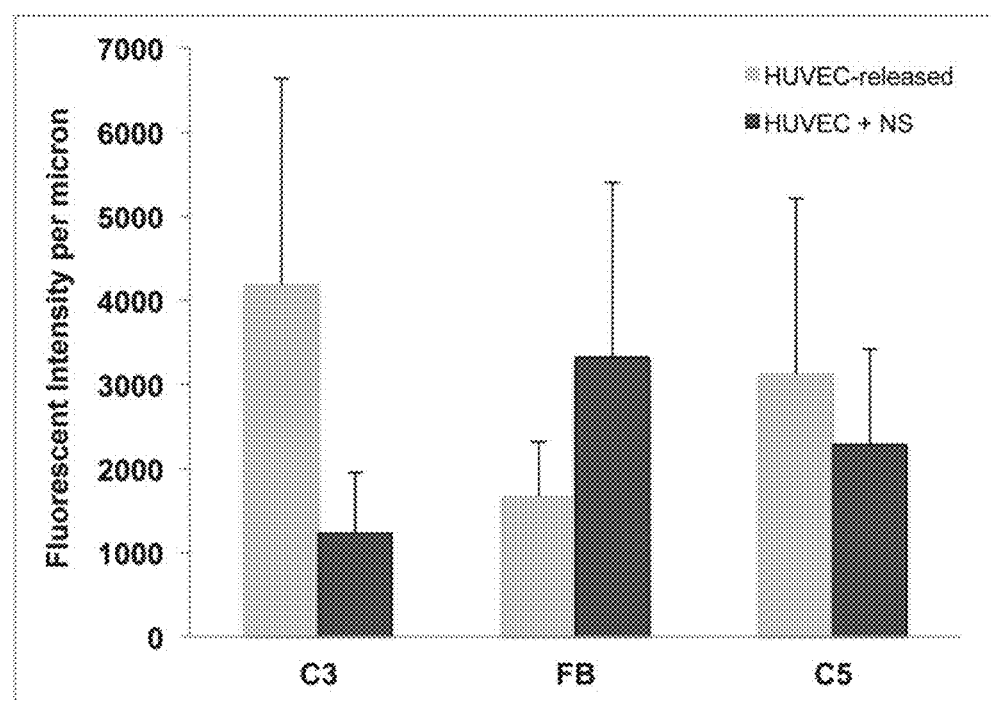

FIG. 14 shows attachment to HUVEC-secreted/anchored ULVWF strings of C3, FB and C5 released from HUVECs+/− added in heated normal serum. Intensities of C3, FB and C5 were measured along histamine-stimulated HUVEC-secreted/anchored ULVWF strings as described in the legend for FIG. 8. Light gray bars represent the binding of exclusively HUVEC-released C3, FB and C5 to ULVWF strings (shown for comparison from FIG. 13), and dark gray bars show the binding of the same components per micron of ULVWF string length in the presence of normal heated serum. Values are means plus SD; N=8-11 strings for each complement component from 5 to 7 experiments for each of C3, FB and C5 and data were compiled from 46 fluorescent images.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

DESCRIPTION

The present disclosure generally relates to a composition comprising a nonfunctional complement factor B (CFB) as a therapeutic agent for treating thrombotic or complement-mediated inflammatory disorders or age-related macular degeneration (AMD).

CFB is a single chain plasma protein (~210 μg/ml, MW 93 kDa). CFB bound to C3b (activated form of C3) is cleaved by factor D (CFD) to the active form Bb by exposing an active serine protease site.

One aspect of the present disclosure is directed to a composition comprising a nonfunctional CFB. As used herein, the term nonfunctional CFB refers to functionally inactive CFB that retains capacity to bind C3b.

CFB may be rendered nonfunctional by heating in a range of from about 45° C. to about 56° C. for a range of about 5 to about 20 minutes. For example, CFB subjected to heating at 56° C. for 15 min becomes functionally inactive while retaining binding capacity to its substrate C3b. Inactive CFB bound to C3b may be used, among other things, to terminate further activation of AP.

In certain embodiments, the CFB may be present in normal human fresh frozen plasma (FFP), the cryosupernatant fraction of FFP (CS), or normal human plasma (NP). In other embodiments, the CFB may be at least partially purified. In another embodiment, the CFB may be a recombinant CFB protein.

In other embodiments, the CFB may be rendered nonfunctional prior to purification or after purification.

Another aspect of the present invention is directed to a process of producing a nonfunctional CFB containing composition comprising inactivating a CFB containing composition.

In one embodiment, the inactivation is by heating. For example, the CFB containing composition may be heated from about 45° C. to about 56° C., from about 50° C. to about 56° C., or 56° C.

The heating may occur for a time sufficient to inactivate CFB. For example, the heating may occur from about 5 minutes to about 20 minutes, from about 10 minutes to about 20 minutes, or for about 15 minutes.

In certain embodiments, the present disclosure provides methods comprising obtaining sterile plasma and heating the plasma for a time and temperature sufficient to inactivate CFB present in FFP. In some embodiments, heat-inactivated CFB may be derived from normal human CS fraction of FFP.

For example, CS may be prepared from FFP by three cycles of: freezing at −80° C., thawing at 4° C., and centrifugation at 15,000×g, 20 min to remove "cryo-precipitated" proteins that are primarily VWF, fibrinogen, and IgM.

In other embodiments, heat-inactivated CFB can be purified or semi-purified from FFP or CS.

Another aspect of the present disclosure is directed to a method of inhibiting or reducing AP activation comprising contacting a nonfunctional CFB containing composition with ECs in an amount sufficient to inhibit or reduce the AP activation.

In the experimental system described below, HUVECs were induced to rapidly secret ULVWF strings while the concentration of concurrently released ADAMTS-13 was restricted by controlling the cell-surrounding volume. Under these conditions, released CP and AP proteins bound to EC-anchored ULVWF strings were fluorescently imaged and quantified. The results indicated that EC-anchored ULVWF strings initiated the activation of the AP (See, e.g., FIGS. 3A-C, 5A, and 8-12).

The mechanism of AP activation is shown in the cartoon FIG. 7B. In the absence of stimulating agents, HUVEC surfaces were devoid of anchored ULVWF strings. Complement components C3, FP, FB, FD, C5, FH and FI were synthesized and released by HUVECs, but did not attach to the EC surface in the absence of secreted and anchored ULVWF strings. Histamine-secreted, anchored ULVWF strings were covered extensively with C3b. C3 was released, activated and amplified by C3 convertases (C3bBb) assembled on the strings. The C3b attachment to the ULVWF strings allowed C3b-FB attachment and FB cleavage and activation to Bb by FD. The assembled C3 convertase (C3bBb) was stabilized by released FP. As C3b amplification continued, additional C3b molecules attached to ULVWF strings near previously string-assembled C3 convertases to form C5 convertase complexes (C3bBbC3b) capable of inducing C5 binding. The binding of FH to some of the ULVWF string-assembled C3bBb complexes caused displacement of Bb and inactivation of C3b by EC-released FI. The binding of C3, CFB and C5 to surfaces is an indication of AP activation.

In parallel experiments, heated serum, diluted to 25% in phosphate buffered saline, pH 7.4 (PBS), was added during HUVEC stimulation, and the CP and AP proteins present in the serum plus those released from the HUVECs were similarly imaged and quantified. The concentrations of CP and AP proteins in serum or plasma (Table 1) are many-fold higher than amounts released by the HUVECs over the experimental time period, yet ULVWF-bound quantities of C3b and C5, the AP proteins associated with initiation of AP activation were not increased (FIGS. 4B-C and 5B). Heat-labile CFB was the only protein involved with AP activation with increased binding (>5-fold) to the EC-anchored ULVWF strings under these conditions (FIGS. 4A and 5B). By comparing the ULVWF binding dating obtained under both conditions, it was concluded that heat-inactivated CFB binding to ULVWF-bound C3b inhibited further activation of AP. The possible mechanism is shown in FIG. 7C.

In the present disclosure, transcripts for complement components C1QB, C2, C3, C4A, C5, CFB, CFD, CFH, CFI and CFP were verified and quantified relative to VWF expression in unstimulated HUVECs using real-time PCR and TAQMAN expression assays. CFD expression in HUVECs was demonstrated and quantified relatie to VWF and after histamine exposure.

AP negative regulatory components CFH and CFI were the only complement genes expressed in HUVECs at levels comparable to VWF. These results indicate that EC synthesis of FH and FI are important for EC self-protection. With exposure to histamine, neither CFH nor CFI expression was increased. HUVEC release of FH was also unaffected (FI protein was not studied). Histamine and other stimulating agents induce secretion of EC-anchored ULVWF strings. The experiments described below indicate that cell-anchored ULVWF strings provide "activating surfaces" that initiate the AP. When ECs are stimulated, function-disabling mutations in CFH or CFI would be expected to allow excessive alternative pathway activation and aHUS episodes more likely to occur. Thrombotic microangiopathy patients have been described with congenital severe (double heterozygous) deficiency of ADAMTS-13 in combination with a heterozygous CFH mutation, or with acquired autoantibodies against both ADAMTS-13 and FH.

Excessive secretion/anchorage of endothelial cell-ULVWF strings occurs in response to endothelial cell stimulation by many agents, including histamine, shiga toxins, and inflammatory cytokines Under our experimental conditions, ADAMTS-13 cleavage of cell-bound ULVWF strings is diminished or delayed, allowing the AP components to attach to, and initiate C3b amplification, by the activating surfaces of the strings.

The experiments described below also demonstrate interactions between HUVEC-anchored ULVWF strings and complement components released from stimulated HUVECs and/or present in heated normal human serum. With the exception of C4, each of the other complement components studied (C1, C2, C3, C5, FB, FD, FH, FI and FP) attached to the HUVEC-anchored ULVWF strings.

The C1q chains within the C1 complex are composed of six collagen-like triple helical structures (Table 2), that may attach to collagen-binding domains in the VWF monomeric subunits of EC-anchored ULVWF strings without C1 activation. C1 of the CP was activated in our studies because C4, either released from HUVECs or present in heated normal human serum, did not attach to EC-anchored ULVWF strings. Only activated C1 (as $C1q_6r_2s_2$) can cleave C4 into C4b, which then becomes capable of binding to nearby surfaces.

There was no evidence of activation of the LP by the HUVEC-anchored ULVWF strings in our studies. The absence of C4 attachment to the EC-anchored ULVWF strings indicates that MBL-MASP did not initiate the LP activation by cleaving C4 to C4b in a process analogous to activated C1.

In the majority of the complement/ULVWF string binding experiments (see, e.g., FIGS. 8-12), ADAMTS-13 was released from the HUVECs (along with complement components) during the 2 min histamine stimulation and the 10 min time period when the cells were incubated with the anti-VWF antibody and fluorescent secondary antibody combination. The cleavage function of the ADAMTS-13 during the 2 min stimulation was suppressed by the use of a relatively large volume of fluid surrounding the cells (1 ml per 4.8 $cm^2$ of surface area) that reduced the affective concentration of released ADAMTS-13 near the surface of the HUVECs as the ULVWF strings were secreted and anchored. After the addition of the anti-VWF antibody, ADAMTS-13 was no longer capable of cleaving the (anti-VWF-coated) ULVWF strings. We make the analogy between restricted of ADAMTS-13 activity (allowing some ULVWF strings to remain uncleaved for our studies) and TTP or other thrombotic microangiopathies with ADAMTS-13 activity that may be inadequate for the rate of EC-secretion/anchorage of ULVWF strings (augmented by cytokines in infection or inflammation).

Stimulation of HUVECs with histamine may result in the release of other EC proteins or altered EC surface protein exposure, in addition to WPB secretion of ULVWF strings. This could account for the background binding (or cell surface binding) of some complement proteins. Our experiments were restricted to the detection and measurement of complement proteins that were bound to the HUVEC-secreted/anchored ULVWF strings. Background subtraction of an equal number of data points, within the same images and in parallel locations, makes it unlikely that the measured intensities of the complement components on the ULVWF strings were the result of random fluorescent binding.

Following the rapid secretion of ULVWF from WPBs, ULVWF multimeric strings remain anchored to EC surfaces until smaller VWF multimers are released into the plasma by ADAMTS-13 cleavage of the EC-secreted/anchored ULVWF. Without an anchor point, the plasma-type small VWF multimers adopt a less accessible globular conformation. Although we did not investigate complement component interaction with plasma-type VWF multimers, it is possible that the C3b recognition sites present on EC-anchored ULVWF strings are not accessible (or less accessible) on the globular conformation of plasma-type VWF.

In our experiments, brief stimulation times and addition of VWF antibodies (that block ADAMTS-13-mediated cleavage) combined to restrict the cleavage of EC-secreted/anchored ULVWF strings by HUVEC-derived ADAMTS-13. We previously demonstrated that the addition of antibodies to VWF does not prevent HUVEC-released ADAMTS-13 from attachment to EC-secreted/anchored ULVWF strings. The current experiments demonstrate interactions between ULVWF strings and complement components released from stimulated HUVECs. With the exception of C4 (a component essential for CP and LP activation), each of the other AP complement components studied (C3, C5, and AP-specific proteins FB, FD, FH, FI and FP) attached to the HUVEC-anchored ULVWF strings.

Small amounts of C3 are released from many cell types (including HUVECs) and can be hydrated to an activated form ($C3-H_2O$) that initiates the conversion of C3 to C3b. Cleavage of C3 releases the small C3a fragment and exposes a thioester in C3b that covalently attaches to "activating surfaces." As shown by our experiments, these include EC-anchored ULVWF strings. Binding affinities of FH for C3b decrease as a result of the structural changes that occur in C3b as it binds to an activating surface. The conformational changes in C3b after its attachment to cell-anchored ULVWF strings may limit the capacity of FH and FI to bind and inactivate C3b. This would favor the assembly of C3 convertase (C3bBb) by FB, FD and FP, and would allow amplification of C3 conversion to C3b and promote additional C3b attachment to the strings.

The assembly and activation of HUVEC-released AP components on EC-bound ULVWF strings would be associated with: HUVEC-released functional FB and C3b binding to each other on the ULVWF strings, followed by FB cleavage to Bb by HUVEC-released FD; the formation of string-bound C3 convertase (C3bBb) complexes; and amplification of C3b generation from C3. In the presence of heated serum, which contains high concentrations of functional C3 and nonfunctional FB, there was a decrease in C3b binding to HUVEC-anchored ULVWF strings compared to experiments when functional C3 and FB were released exclusively from HUVECs. We conclude that a considerable quantity of C3b binding to the strings, using HUVECs alone, was the result of string-bound C3bBb (C3 convertase) assembly and amplification of C3b generation from HUVEC-released C3. In the presence of non-functioning FB in the heated serum, a poorly functioning C3 convertase assembled on the ULVWF strings.

Detection on the EC-anchored ULVWF strings of HUVEC-released C3, FB and C5 implies that both the alternative pathway C3 convertase and the C5 convertase assemble on EC-secreted/anchored ULVWF strings. The attachment of HUVEC-released C3 (after cleavage to C3b) on ULVWF strings was ~30% greater than the attachment of HUVEC-released C5 to the strings. As the number of C3b molecules attached to an activating surface increases to form C3bBbC3b complexes, then C5 binds with higher affinity to the accumulating C3b molecules. These data are compatible with the formation of some C3bBbC3b (C5 convertase) complexes capable of binding C5 on the ULVWF strings. This was demonstrated conclusively in images of C3 and C5 attached to the same points along HUVEC-secreted/anchored ULVWF strings.

The assembled C3 convertase (C3bBb) and C5 convertase (C3bBbC3b) complexes on EC-anchored ULVWF strings may generate TCCs [$C5b678(9)_n$]. The C5 convertase cleaves C5 to C5b en route to the formation of C5b678 complexes, which can be inserted into cell membranes to associate with multiple C9 molecules. HUVEC membranes have CD46, thrombomodulin and DAF (decay-accelerating factor; CD55) to prevent surface C3 and C5 convertase assembly or persistence. ECs also have cell surface CD59 and secrete vitronectin (S-protein) and clusterin to protect against TCC formation. We could not detect surface TCCs or soluble SC5b-9 complexes in our cell experiments, and we did not observe HUVEC lysis. If terminal complexes were generated during the short duration of our experiments, the amounts may have been too low to be detected by the polyclonal and monoclonal anti-SC5b-9 antibodies used in our assays. EC regulatory proteins may have protected HUVECs against lysis by any small quantities of TCCs were generated during our experiments.

Possible targets of any TCCs generated by activation of the alternative complement pathway on endothelial cell secreted/anchored ULVWF strings include microbes and injured or defective tissue (including endothelial) cells. In addition to histamine, calcium ionophore and phosphodiesterase inhibitors, ULVWF strings are secreted from endothelial cells that have been stimulated by cytokines (TNFα, IL-6, IL-8) associated with infection and inflammation.

We have demonstrated the interaction and probable assembly/activation of alternative complement components on EC-secreted/anchored ULVWF strings. The findings may have pathophysiological and potential therapeutic importance in thrombotic and complement-mediated inflammatory disorders, and provide one possible molecular mechanism for recent observations suggesting clinical links between different types of thrombotic microangiopathies. Possible new therapy, in addition to a monoclonal antibody to C5 currently available, includes blockade of the AP C3 convertase using heat-inactivated FB that is described above.

Another aspect of the present invention is directed to a method of preventing or treating an individual at risk for at least one thrombotic or complement-mediated inflammatory disorder, comprising administering to the individual an effective amount of a composition comprising a nonfunctional CFB.

The compositions of the present disclosure may be used for infusion or with plasma exchange as therapy for patients with clinical characteristics of thrombotic microangiopathies resulting from excessive AP activation due to loss of complement regulation from mutations or autoantibodies against components or receptors of AP.

There are multiple reports of complement activation in patients with ADAMTS-13-deficient TTP. One study of 23 TTP patients with antibodies to ADAMTS-13 reported increased activation in CP, LP, and AP. In another study of 8 TTP patients (3 with and 5 without antibodies to ADAMTS-13), only AP activation was found. A recently described ADAMTS-13-deficient TTP patient who was unresponsive to therapy with plasma exchange recovered with the addition of a monoclonal antibody to C5 (eculizumab). We have, furthermore, recently seen a 3-month-old infant with a severe episode of HUS in association with an ADAMTS-13 level of 39% (pre-transfusion sample measured by FRETS-VWF73) and a FH value of 76 µg/ml (normal neonate range is 170-397 µg/ml). These are all plausible clinical examples of complement activation by uncleaved, EC-anchored ULVWF strings.

Some aHUS patients with only mild or moderate deficiencies of ADAMTS-13 may have sufficient reduction or delay in the cleavage of EC-anchored ULVWF strings, and consequently, AP activation. Examples include one aHUS patient with a gain-of-function C3 mutation, and 3 of 7 aHUS patients with loss-of-function thrombomodulin mutations (causing less effective C3b inactivation by FH and FI) who were reported to have "abnormal" ADAMTS-13 activity. In addition, individuals with AP deficiencies or defects may be more prone to an episode of aHUS during infections or other clinical events associated with increased inflammatory cytokines that initiate the cycle of EC stimulation and secretion of anchored-ULVWF multimeric strings, excessive platelet adhesion, and AP activation.

The current treatment of FFP (or CS) infusion provides normal concentrations of complement plasma proteins that include AP negative regulatory proteins factor H (CFH) and factor I (CFI), and late terminal component inhibitor S-protein. FFP infusion reduces AP activation in patients deficient in plasma negative regulatory proteins but is limited therapeutically in patients with gain-of-function mutations in C3 and CFB or defects in complement receptors such as thrombomodulin (THBD), CD55, and CD59. In contrast, the infusion of heat-inactivated FFP according to the present disclosure, contains inactive CFB that competitively binds to C3b and terminates further activation of the AP. The heat-inactivated FFP actively inhibits activation of AP (via nonfunctional CFB) while retaining fully functional CFH and CFI which are uncompromised by 56° C. heating. Heat-inactivated FFP also may have the advantage of being composed of fully human components, as well as offer a simple, low cost process.

In certain embodiments, the disorder is a thrombotic microangiopathy. Examples of thrombotic microangiopathies include, but are not limited to, TTP, D-HUS, and aHUS.

Examples of other complement-mediated inflammatory disorders include, but are not limited to, lupus erythematosus, glomerulonephritis, paroxysmal nocturnal hemoglobinuria, and inflammatory bowel disease.

In other embodiments, the present disclosure provides using the heated FFP as infusion therapy for age-related macular degeneration (AMD). AMD is a neurodegenerative disease causing blindness characterized by excessive retina complement deposition and is associated with defects in AP genes CFH, C2/CFB and C3.

To facilitate a better understanding of the present invention, the following examples of certain aspects of some embodiments are given. In no way should the following examples be read to limit, or define, the entire scope of the invention.

EXAMPLES

Materials and Methods

Complement Components and Antibodies.

Goat polyclonal antibodies to individual human complement components, purified human complement proteins, and human sera depleted of each specific complement factor were obtained from Complement Technology (Tyler, Tex.). Monospecific reactivity of each complement antibody was verified by Western blotting using sets of purified complement proteins, normal sera and component-specific depleted sera. Properties of some complement proteins used in this application are shown in Table 1.

TABLE 1

Properties of Complement Proteins

| Protein | Plasma/Serum, µg/ml | Molecular Weight, kDa | Secreted Structure* |
|---|---|---|---|
| C1q | 70-140 | 460 | 6 (A-B) Disulfide-linked chains, 51 kDa 3 (C-C) Disulfide-linked chains, 48 kDa |
| C2 | 11-35 | 102 | Single chain |
| C3 | 1000-1500 | 185 | 2 Disulfide-linked chains: 110; 75 kDa |
| C4 | 250-550 | 205 | 3 Disulfide-linked chains: 97; 75; 33 kDa |
| C5 | 55-113 | 190 | 2 Disulfide-linked chains: 115; 75 kDa |
| FB | 170-258 | 93 | Single chain |
| FD | 1-2 | 24 | Single chain |
| FH | 250-564 | 150 | Single chain |
| FI | 35 | 88 | 2 Disulfide-linked chains: 50; 38 kDa |
| FP | 4-6 | 53 | 2, 3, or 4 Aggregates of 53 kDa |

*Molecular mass band position in unreduced SDS-acrylamide gels.

Each polyclonal complement antibody was reactive against the intact component protein and the corresponding cleavage fragments. Complement C3 was also identified using a combination of mouse anti-human C3b (clone 755) and anti-human C3 (clone 10A1) monoclonal antibodies (Pierce/Thermo Scientific) in the fluorescent microscope experiments. The average serum concentrations of complement proteins in this study are: C3 1300 µg/ml; C4 400 µg/ml; C5 75 µg/ml; FB 200 µg/ml; FD 2 µg/ml; FH 500 µg/ml; FI 35 µg/ml; and FP 5 µg/ml.

Western Immunoblots.

Denatured, non-reduced samples in sodium dodecyl sulfate (SDS) were electrophoresed into 7.5% or 4-15% polyacrylamide gels (BioRad) and transferred to PVDF membranes. Membranes were overlaid separately with polyclonal goat antibodies to each complement component followed by secondary rabbit anti-goat IgG-HRP plus StrepTactin-HRP conjugate and chemiluminescent reagents (WesternC, BioRad) before digital imaging (ChemiDoc XRS, BioRad). Each blot in FIG. 2A contains lanes with: 50 ng of a purified complement protein (Std), normal serum (NS) containing 50 ng of the specific complement component, an equal volume of specific complement component-depleted sera and StrepTactin-labeled protein standards. Quantitative exceptions to the proceeding were: In the C2 blot the NS lane contains 40 ng C2 (C2 serum conc. ~20 ng/µl); in the FD blot the Std lane contains 159 ng FD and NS lane contains 4 ng FD (FD serum conc. ~2 ng/µl) and in the FP blot the NS lane contains 10 ng FP (FP serum conc. ~5 ng/µl). Goat antibody to FD was pre-adsorbed with FD-depleted sera using a 1:4 ratio.

Human Umbilical Vein Endothelial Cells (HUVECs).

Primary HUVECs were isolated from umbilical veins as previously described. Cells were seeded in flasks or on glass coverslips for microscopy experiments and grown in Endothelial Basal Medium (EBM, Lonza, Hopkinton, Mass.), supplemented with 3% penicillin-streptomycin (P/S), 0.2 mM L-glutamine and Low Serum Growth Supplement (Invitrogen). HUVECs used for RNA isolation were incubated for 24 hours in serum-free EBM plus insulin-transferrin-selenium (ITS, Invitrogen). HUVEC RNA isolated to calculate efficiencies for CFD and CFP were incubated for 24 hours±100 µM histamine followed by 24 hours in serum-free EBM plus ITS.

Fibroblasts.

Human adult dermal fibroblasts were purchased from American Type Culture Collection (Manassas, Va.) and maintained in Dulbecco's Modified Eagle's Medium (DMEM) plus 3% P/S, glutamine and 10% fetal bovine serum (Atlanta Biological). Prior to RNA extraction, fibroblasts were incubated for 24 hours±100 ng/ml lipopolysaccharide (LPS, Sigma) followed by 24 hours in serum-free DMEM plus ITS±100 ng/ml LPS.

Relative Quantitative Gene Expression.

HUVEC and fibroblast RNA was isolated using TRIzol (Invitrogen), chloroform extraction and isopropanol precipitation. RNA integrity was verified by 260/280 optical density ratios and 1%-agarose-formaldehyde electrophoresis, and was reverse transcribed using SuperScript III Supermix (Invitrogen). Samples (100 ng cDNA) were amplified in quadruplicate by real-time polymerase chain reaction (PCR) under conditions: 95° C. for 3 min, 40 cycles of (10 sec at 95° C., 10 sec at 55° C., 30 sec at 72° C.), and 95° C. for 10 sec followed by melting curves from 65° C. to 95° C. (CFX96, BioRad). Amplified products were detected using TAQMAN Gene Expression Assays (with 6-carboxyfluorescein-labeled probes that span target exon junctions) and Fast Advanced Master Mix (Life Technologies, Carlsbad, Calif.). Efficiencies (E) were determined by amplification of 100 ng-0.01 ng of cDNA, calculating the slope of the line after plotting the threshold cycle ($C_T$) versus ng of cDNA and using equation (1).

$$E = 10^{\left(\frac{-1}{slope}\right)} \quad (1)$$

$$\text{Ratio} = \frac{(E_{Target})^{\Delta C_T(control-treated)}}{(E_{Ref})^{\Delta C_T(control-treated)}} \quad (2)$$

To calculate primer efficiencies, $C_T$ detection of at least three 10-fold dilutions of cDNA are required for each probe. PCR products for HUVEC C2 and C3 were detected within 40 cycles with 100 ng of cDNA but were below detection with initial amounts of 10 ng cDNA or lower. To alleviate this problem, RNA from cultured human dermal fibroblasts with/without exposure to LPS was isolated and the cDNA was used to calculate the probe efficiencies for C2 and C3. Fibroblast expression of C2 was 3-fold higher and C3 was 39-fold higher than in HUVECs. The addition of 100 ng/mL LPS to fibroblast cultures increased C2 levels by 1.4-fold and increased C3 levels by 19-fold, resulting in sufficient mRNA to calculate probe efficiencies for C2 and C3 (Table 2).

TABLE 2

Fold increases of C2 and C3 mRNA expression

|  | C2 | C3 |
|---|---|---|
| Fibroblasts relative to HUVECs | 3.13 ± 0.15 | 38.99 ± 0.15 |
| Fibroblasts + LPS* | 1.43 ± 0.23 | 19.18 ± 0.12 |

*Fold-increases induced with 100 ng/ml LPS.

Although HUVEC mRNA levels for C1QB, CFD and CFP were comparably as low as C2 and C3, the transcripts for C1 QB, CFD and CFP increased enough in HUVECs exposed to histamine to detect and calculate efficiencies for these probes directly from HUVEC mRNA (FIG. 1). Although HUVEC mRNA levels for CFD and CFP were comparably as low as C3, the transcripts for CFD and CFP increased 2- and 3-fold, respectively, in HUVECs exposed to histamine. The RNA isolated from the histamine stimulated HUVECs was used to calculate efficiencies for the CFD and CFP probes.

The fold-changes in HUVEC mRNA gene expression with exposure to histamine (treated) and without histamine (control) were calculated with equation (2) using GAPDH as the reference gene. The standard deviation in gene expression assays (S) was determined by the equation: $s = \sqrt{s_1^2 + s_2^2}$ where $S_1$ and $S_2$ are the standard deviations of quadruplicate $C_T$ measurements for the reference and target genes.

Factor H Fluorescent Immunoassay.

Black 96-well plates were coated with 2 µg/ml goat anti-human FH in bicarbonate buffer, pH 9.6 overnight (ON) at 4° C. Phosphate buffered saline (PBS)-Triton-X (T) washed wells were blocked ON with 1% immunoglobin-free bovine serum albumin (BSA) in BSA/PBS, followed by ON incubation with serial dilutions of purified FH protein in BSA/PBS (for standard curve) or HUVEC conditioned (serum-free media) samples. PBS-T washed wells were further incubated with mouse monoclonal antibody to human FH (Pierce, Thermo Scientific) and secondary mouse IgG-HRP. Fluorescence was measured in the Infinite M200 Pro (Tecan, Research Triangle Park, N.C.) after the addition of fluorescent substrate ADHP (10-Acetyl-3,7-dihydroxyphenoxazine; AnaSpec, Fremont, Calif.) with excitation at 530 nm and emission at 590 nm.

Fluorescent Microscopy Studies.

Fluorescent images were acquired using IP Lab software version 3.9.4r4 (Scanalytics, Inc., Fairfax, Va.) on a Nikon Diaphot TE300 microscope equipped with a CFI Plan Fluor 60× oil N.A. 1.4 objective plus 10× projection lens (Nikon, Garden City, N.Y.), SensiCamQE CCD camera (Cooke Corp., Romulus, Mich.), motorized stage and dual filter wheels (Prior) with single band excitation and emission filters for FITC/TRITC/CY5/DAPI (Chroma, Rockingham, Vt.).

VWF, complement proteins and ADAMTS-13 were imaged using the following primary antibody and fluorescent secondary antibody pairs: polyclonal rabbit anti-human VWF (Ramco Laboratories, Sugarland Tex.) plus Alexa Fluor 488 (green) chicken anti-rabbit IgG (Invitrogen); goat polyclonal antibodies to individual human complement components plus Alexa Fluor 594 (red) donkey anti-goat IgG (Invitrogen); and polyclonal goat anti-human ADAMTS-13 (anti-CUB2, Bethyl Laboratories) plus Alexa Fluor 594 (red) donkey anti-goat IgG (Invitrogen). Complement C3 was also imaged using a combination of mouse anti-human C3b (clone 755) and anti-human C3 (clone 10A1) monoclonal antibodies (Pierce/Thermo Scientific) plus Alexa Fluor 647 goat anti-mouse F(ab')$_2$ IgG (Invitrogen). Cell nuclei (blue) were detected with 1 nM 4,6 diamidino-2-phenylindole (DAPI).

Heat-Inactivated Normal Serum.

Sera from normal consenting donors collected under a protocol approved by the Rice University Institutional Review Board were pooled and stored at −80° C. until use. Before cell experiments, pooled serum was heated to 56° C. for 15 min (heated serum) and diluted to 25% in PBS.

Interaction of HUVEC-Secreted/Anchored ULVWF Strings with Complement Components Released from HUVECs or Present in Heated Normal Serum.

HUVECs on coverslips were washed with PBS and stimulated with either: 100 µM histamine in 1 mL of PBS for 2 min followed directly by immunostaining; or 100 µM histamine in 25% heated serum/PBS for 5 min followed by 4 PBS washes before staining. The cytokines TNFα, IL-8 and IL-6 (+ receptor), shiga toxins-1 and -2 and histamine stimulate ECs to secrete surface-anchored ULVWF strings.Histamine was used in this study to stimulate the HUVECs.

HUVECs stimulated under both conditions were then stained with rabbit anti-VWF plus anti-rabbit IgG-488 for 15 min, fixed for 10 min with 1% p-formaldehyde and then stained separately with goat anti-human complement component antibodies plus anti-goat IgG-594 for 10 min. Cell nuclei were detected with DAPI. In some experiments 52 µg/ml of purified FB were added to the heated serum, a concentration similar to the FB concentration in PBS-diluted heated serum (Table 1). For un-stimulated control experiments, HUVECs on coverslips were incubated for 5 min with 25% heated serum/PBS, washed 4× with PBS, immunostained with rabbit anti-VWF plus anti-rabbit IgG-488, and then immunostained separately with goat complement antibodies plus anti-goat IgG-594 and with DAPI.

Evaluation of HUVEC-Secreted/Anchored ULVWF Strings and Complement Component Interaction.

HUVEC-anchored ULVWF strings detected with rabbit anti-VWF plus fluorescent anti-rabbit IgG-488 were electronically traced in 488-nm (green)-captured images at 600× magnification and the emitted fluorescent intensity was measured at each pixel (x, y) point along the line. The coordinates of the traced ULVWF line were transferred to the corresponding 594-nm (red)-captured images obtained using specific polyclonal goat antibodies against single complement components plus fluorescent anti-goat IgG-594. The fluorescent intensity at 594-nm from each detected complement component was measured along the transferred line coordinates. In order to determine background 594-nm intensity, the line coordinates were trans-located ~20 pixels parallel (~2.3 µm) to its original position within this same image and the fluorescent intensity was measured. The quantity of each complement component attached to the ULVWF strings was expressed as the percentage of points measured (at 594-nm) with fluorescent intensities >500 units after background subtraction. Image dimensions: 78 µm×58 µm, or 688 pixels×512 pixels with 1 pixel=0.113 µm.

$$C \text{ protein binding} = \frac{\text{Intensity}_{594} - \text{Background Intensity}_{594}}{\text{ULVWF length, microns}}$$

Heat-Denatured ADAMTS-13 Attachment to ULVWF Strings.

HUVECs on coverslips were stimulated with 100 µM histamine in 25% heated serum/PBS for 5 min, and then stained with rabbit antibodies to VWF followed by goat anti-ADAMTS-13 plus anti-goat IgG-594 and DAPI. ADAMTS-13 binding to ULVWF strings was evaluated using methods that were identical to those used for the complement proteins.

Fluorescent Emission "Bleed-Through" Controls.

We did not detect any of the complement components in HUVEC Weibel-Palade bodies. For C3, this is in agreement with Misumi, et al., who previously showed that precursor C3 protein, after furin cleavage, is not sorted to a storage vesicle. Non-stimulated HUVECs were fixed in 1% p-formaldehyde and treated with 0.02% Triton-X to allow internal staining. In every control slide, VWF in Weibel-Palade bodies was detected with rabbit anti-VWF plus secondary anti-rabbit IgG-488 and cell nuclei were stained with DAPI. Single slides were then stained with one of the goat antibodies to individual human complement components plus secondary anti-goat IgG-594.

Unstimulated HUVECs were fixed and treated with Triton-X to allow intracellular staining, and then immunostained with anti-VWF antibody plus 488-secondary antibody. VWF staining was followed by addition of each complement antibody plus 594-secondary antibody in separate experiments. Because WPBs contain a high concentration of VWF and are devoid of complement components, these organelles were used to demonstrate the separation of fluorescent signals obtained at 488 and 594 nm in our microscope system. The fluorescent intensity at 594 nm (red), used for detection of the complement proteins attached to HUVEC-anchored ULVWF strings, was not a result of fluorescent "bleed through" from the 488-nm channel (green) used for VWF detection. This was demonstrated by the following experiments. Non-stimulated HUVECs were treated with 0.02% Triton-X to allow internal WPB staining, followed by: (1) staining with rabbit antibodies to VWF plus secondary anti-rabbit IgG-488; and (2) goat antibodies to AP components plus secondary anti-goat IgG-594. Intensities were measured across WPBs located by high levels (up to 2500 fluorescence intensity units) of VWF-positive fluorescence in 488-nm images (green), and in identical locations in 594-nm (red) images. The levels measured in the 594-nm channel were <100 fluorescence intensity units per micron, confirming that there was little or no fluorescent "bleed through" during image acquisition for the experiments with ULVWF strings (green) and the different complement components (red) (FIG. 6C-D).

Results: HUVEC Gene Expression of Complement Components

Gene Expression of CFD in HUVECs.

Transcripts for CFD were identified in HUVECs for the first time in this study using RT-PCR with probes recognizing only cDNA transcribed from mature mRNA in order to exclude genomic DNA. The presence of HUVEC-synthesized and released FD was important for demonstrating alternative complement activation in experiments using HUVECs alone, without the addition of serum. In the absence of FD, neither cleavage of C3b-bound FB to Bb nor subsequent amplification of C3b activation from C3 by C3 convertase (C3bBb) could occur. In the experiments to follow, the attachment of complement components to HUVEC-secreted/anchored ULVWF strings is described using HUVECs in both the absence and presence of heated normal human serum.

Expression of Complement Components Relative to VWF.

Alternative pathway regulatory components CFH and CFI were the only complement genes expressed in HUVECs near levels of VWF expression; CFH was similar and CFI was ~6-fold higher. In contrast, expression levels of C5, C4 and CFB were 10-, 50- and 70-fold lower, respectively, and C3, C2, C1 QB (beta chain of C1q), CFD and CFP were about 1000-fold lower than VWF expression levels (FIG. 1A).

Transcripts for the VWF protease, ADAMTS-13, which is also produced and released from HUVECs, were ~10-fold lower than VWF transcripts. ADAMTS-13 was included as an additional indicator of EC transcription.

Changes in HUVEC Complement Component Expression with Histamine Exposure.

HUVECs were incubated for the first 24 hours in complete serum-containing medium in the presence or absence of histamine, followed by 24 hours in serum-free medium with or without histamine. HUVEC expression levels of AP components CFD, CFP and CFB increased with histamine stimulation. CFD mRNA levels doubled (2.2-fold increase), and CFP levels increased 3-fold. CFB was increased 7-fold in HUVECs exposed to histamine compared to un-stimulated cells, and FB protein released over 120 hours from histamine stimulated HUVECs then became detectable by Western blotting [FIG. 1B, inset (a)]. Histamine did not affect C3 and C5 expression: HUVEC C5 was moderately depressed (0.7-fold) and C3 expression was unchanged (FIG. 1B).

Expression levels of the AP regulatory genes, CFI and CFH, were unchanged by histamine exposure. In contrast to FB, because CFH transcripts are ~100-fold higher than CFB, FH released from un-stimulated HUVECs was detectable by 7 hours with Western blot analysis. Consistent with stable CFH transcription, release of FH was also unaffected by HUVEC exposure to histamine over time periods ranging from 30 min to 96-hours [FIG. 1B, inset (b) and FIG. 1C].

In histamine-exposed HUVECs, mRNA levels of CP components C2 (1.9-fold) and C4 (1.5-fold) were only slightly up regulated while C1QB levels were increased 15-fold Histamine also induced increased HUVEC message levels of VWF (2.7-fold) and ADAMTS-13 (1.6-fold) (FIG. 1B).

Results: Complement Protein Binding to ULVWF Strings: Comparison of Complement Proteins Released Exclusively from HUVECs with Complement Proteins from Heated Serum in Addition to Those Released from HUVECs Overview of Complement Binding to ULVWF Strings.

In the presence of the EC stimulatory substance, histamine, HUVECs rapidly (within 2 min) secrete ULVWF strings from their storage vesicles [Weible-Palade bodies (WPBs)] onto cell surfaces. We have previously demonstrated the release of anchored ULVWF strings from histamine stimulated HUVECs under non-flowing, static experimental conditions. The static conditions allow the accumulation of HUVEC-released proteins that would be washed away under flowing conditions. Antibodies to VWF were added 2 min after the ECs were stimulated with histamine, to identify fluorescently the ULVWF strings and to prevent cleavage of the secreted/anchored ULVWF strings by HUVEC-released ADAMTS-13. Over the following 15 min complement components released from the HUVECs attached to the EC secreted/anchored ULVWF strings.

The polyclonal antibodies made against human complement proteins used in fluorescent microscopy experiments specifically identify individual complement components, as demonstrated by Western blots (FIG. 2 and Table 1). Fluorescent imaging was used to analyze complement protein attachment to HUVEC-secreted and anchored ULVWF strings. The serum samples applied to the gels (usually 20-25 µg/lane) contained many-fold higher amounts of protein than were secreted by the HUVECs during our experiments; nevertheless, bands for other proteins other than the specific complement factors (and corresponding cleavage fragments) were not detected by the individual mono-specific polyclonal antibodies made against the different complement components. A degradation product of C4 is detected in the C4-depleted serum and two degradation products of C5 are detected in the C5-depleted serum.

In order to analyze FD and FP in serum, the quantities of protein in gel samples were increased even further to ~100 µg/lane. This is the maximum amount of protein per gel lane that can enter completely, and be separated effectively, in our electrophoresis system. The FD in the serum samples was still undetectable because of the low FD serum concentrations (1-2 ng/µl). In the blot detected with antibody to FP, the migration of the FP standard was altered slightly by the high albumin concentration present in the FP-depleted sample in the adjacent lane. The FP in normal serum (4-6 ng/µl) was barely detectable.

The complement components in this application were not detected in HUVEC WPBs and, therefore, it is improbable that ULVWF multimers were pre-bound with complement proteins prior to their secretion. The technical details are in "Fluorescent emission 'bleed-through' controls" in the Material and Methods section.

The complement proteins analyzed were either released exclusively from HUVECs or were added in diluted, heated normal human serum to the HUVECs. Fluorescent images of FB, C3, C5, FI and C4 attachment to HUVEC-anchored ULVWF strings are shown in FIG. 3 (exclusively HUVEC-released complement components) and in FIG. 4 (HUVEC-released complement components plus complement components from heated serum). The attachment data under both conditions are summarized in FIG. 5. Additional attachment images and image controls are detailed in FIG. 6.

In the initial fluorescent imaging experiments, the complement proteins analyzed for attachment to HUVEC-secreted and anchored ULVWF strings were synthesized and released exclusively from HUVECs and accumulated under the non-flowing experimental conditions. Neither a serum nor plasma source of the components was present in the experiments. Fluorescent images and fluorescent intensity graphs of complement components attaching along the HUVEC-secreted/anchored ULVWF strings are shown in FIGS. 8-12, and the quantitative attachment data are summarized in FIG. 13.

AP Component Attachment to ULVWF Strings.

FB binding capacity to the HUVEC-anchored ULVWF strings was not destroyed by heating to 56° C., in contrast to FB functional activity. Heat-inactivated FB attached to 36% of the total lengths of the strings, a 6-fold increase over FB released exclusively from HUVECs (FIGS. 3A, 4A and 5). There was no increase in FB binding to anchored ULVWF strings with the addition of purified, functional FB to heated serum (data not shown). This result indicates that FB in heated serum, even though lacking functional activity, is capable of binding to the ULVWF strings as effectively as purified, unheated FB.

C3 was the component released exclusively from HUVECs that bound most extensively to secreted/anchored ULVWF strings, attaching to >30% of the string lengths measured. HUVECs synthesize only low levels of C3 as demonstrated by C3 mRNA levels (FIG. 1A). The high percentage of C3 attached to ULVWF strings indicates that most of HUVEC-released C3 attached to the strings. Despite the high concentration of C3 in normal serum (~1 mg/ml, Table 1), less than half as much C3 from heated serum attached to HUVEC-anchored ULVWF strings compared to C3 released exclusively from HUVECs. This reduction may be the consequence of enzymatically-inactive FB from heated serum competitively binding to C3b on the strings and preventing the amplification of C3b by forming inactive C3b-FB complexes instead of active C3 convertases (C3bBb) (FIGS. 3B, 4B and 5).

In either experiments with HUVEC-released components alone, or with heated serum addition, ~12% of EC-anchored ULVWF strings were covered by C5. The addition of heated serum provided more functional C3 and C5, but only non-functional FB, and the percentage of bound C5 did not change (FIGS. 3C, 4C and 5). This result suggests that the failure to generate additional C3b by C3 convertases attached to the ULVWF strings (due to the non-functioning C3b-FB complexes) also limited C5 binding to the ULVWF strings, and consequently, reduced C5 convertases (C3bBbC3b) formation because C5 only binds to C3b molecules within or adjacent to C3bBbC3b complexes.

The attachment of FI to EC-anchored ULVWF strings was similar, either with or without the addition of heated serum (11%). In contrast, about twice as much FH released exclusively from HUVECs (17%) attached to the ULVWF string lengths compared to FH attachment with the addition of heated serum (8%) (FIGS. 3D, 4D and 5). The relatively reduced FH attachment with heated serum may be the result of structural changes in heat-inactivated FB (within C3b-FB complexes on the ULVWF strings) that interfered with (heated) FB displacement by FH. Factor H, in contrast to FB, is structurally and functionally resilient to heating.

Each of the AP-specific components FB, FD and FP (the positive AP regulatory protein) bound to the ULVWF strings with average fluorescent intensities per micron of ULVWF string length that were 30- to 50-fold higher than values for the classical pathway-specific component C4 (C4 data shown in FIG. 12). FB, reactive only with activated C3b not intact C3, bound most extensively to the ULVWF strings (>1600 fluorescent intensity per micron) (FIG. 8A). The measured fluorescent intensities for FP and FD (~1000 units/micron) were also high, considering the low expression levels of these components in HUVECs (as shown in FIG. 1). This demonstrates a high affinity of FD and FP for HUVEC-anchored ULVWF strings (FIG. 8B-C).

Fluorescent intensities measured for the AP-specific negative regulatory components FH and FI along the ULVWF strings were similar to each other (FIG. 9A-B, 2400 units/ micron), averaging ~30 to 40% lower than the fluorescence measured for the most extensively bound complement components, C3 and C5, as discussed below. FH displaces FB or Bb bound to C3b, thereby preventing further AP activation. FH also acts as a cofactor for the FI proteolysis and inactivation of C3b.

CP Component Attachment to ULVWF Strings.

Heating serum at 56° C. inactivates CP components C1 and C2; however, both components retained ULVWF string binding capacity. C1q from heated serum attached to 32% of HUVEC-anchored ULVWF string lengths, >2-fold increase over the amount that attached from HUVEC release alone (FIG. 5). C1q contains the binding/recognition sites of C1 ($C1q_6$, $C1r_2$, $C1s_2$) that attaches the component to a variety of protein domains, regardless of activation. Upon activation, C1s subunits cleave C4 into functional C4b that binds to nearby surfaces by an exposed thioester. There was almost no binding of C4 to HUVEC-anchored ULVWF strings, in the absence or with the addition of heated serum with ~600 µg/ml functional C4 (Table 1, FIGS. 3E, 4E and 5). In the heated serum, C1s was inactivated (by the heating), and C4 was not cleaved to a function form. In the experiments with exclusively HUVEC-release proteins, the near-absence of C4 binding substantiates that the C1 attached to EC-anchored ULVWF strings did not activate either the classical or the lectin complement pathways.

Additional functionally inactive C2 provided from heated serum attached to 10% of HUVEC-anchored ULVWF string lengths, an increase over the 4% of string attachment by functional C2 released only from HUVECs. These results imply that the heat-inactivated C2 was equally, or possibly more capable of binding to ULVWF strings as was functional C2 released from HUVECs (FIG. 5). The attached C2 was not assembled into C4b2a complexes (the classical pathway C3 convertase) because C4 binding to EC-anchored ULVWF strings did not occur under any of our experimental conditions.

HUVEC-released C3 (in the form of C3b) was the complement component that bound most extensively to the secreted/anchored ULVWF strings, with average intensities of >4000 fluorescent intensity units per micron of ULVWF string length (FIG. 10A). HUVECs synthesize low levels of C3, as demonstrated by C3 mRNA levels in FIG. 1; however, the extensive attachment of C3 indicates a high level of affinity of C3 for the HUVEC-anchored strings.

C5 released from HUVECs was the second most abundant complement component detected along HUVEC-anchored ULVWF strings (>3000 fluorescent intensity units per micron) (FIG. 10B).

The binding of C5 suggests that C5 convertases (C3bBbC3b) have formed on the ULVWF strings because C5 binds preferentially to C3b molecules within or adjacent to C3bBbC3b complexes. This interpretation was confirmed by the demonstration that C3 and C5 often attached to the same positions on HUVEC-secreted/anchored ULVWF strings (FIG. 11). In these experiments, C3 was detected using a combination of two mouse monoclonal antibodies. One of the monoclonal antibodies was reactive only with C3b.

Classical and lectin pathway complement component C4 does not attach to HUVEC-secreted/anchored ULVWF strings.

In contrast to C3 and C5, and the AP-specific components, there was almost no binding of classical component C4 to ULVWF strings. The average C4 fluorescent intensity measured along the strings was 100-fold less per micron than the intensities measured for C3 or C5 (FIG. 12).

Quantitative Summary.

The quantitative data of exclusively HUVEC-released complement component binding to EC-secreted/anchored ULVWF strings is summarized in FIG. 13. The fluorescent intensity at 594 nm (red), used for detection of the complement proteins attached to HUVEC-anchored ULVWF strings, was not a result of fluorescent "bleed through" from the 488-nm channel (green) used for VWF detection. The experimental details that confirm this conclusion are in the Materials and Methods section.

Complement Components do not Bind to Surfaces of Unstimulated HUVECs.

Neither C3 nor C5 exclusively released from the HUVECs, or added in heated serum was detected on unstimulated HUVEC surfaces devoid of ULVWF strings. The absence of C3 and C5 on HUVEC surfaces, along with the absence of anchored ULVWF strings, indicates that C3 and C5 were only bound to HUVEC-secreted/anchored ULVWF strings in our experiments (FIG. 6E-F).

Additional Interpretation of Results and Controls.

The binding data of complement components released exclusively from HUVECs were especially important because each complement protein studied was secreted along with the HUVEC-anchored ULVWF strings. The complement proteins were produced and released by the HUVECs, and were not purified from plasma or produced as recombinant proteins. The addition of heated serum provided higher concentrations of functional complement components present in normal plasma with the exceptions of FB, C1 and C2 that are (functionally) heat-labile. Heating the serum to 56° C. was required in order to inactivate the VWF proteolytic activity of ADAMTS-13. Unheated ADAMTS-13 is capable of cleaving HUVEC-anchored ULVWF strings within 2 min under our static experimental conditions (without the application of shear stress or addition of chemicals).

Heat-inactivated ADAMTS-13 binds to HUVEC-anchored ULVWF strings, as do functionally heat-inactivated FB, C1q and C2 (FIG. 6A-B).

Our data on complement component binding indicate that initiation and assembly of alternative complement C3 and C5 convertases occurred on HUVEC-anchored ULVWF strings. The fluorescent detection of the complement proteins attached to the anchored ULVWF strings was not a result of fluorescent "bleed through" from the channel used to detect VWF (FIG. 6C-D). Additionally, neither C3 nor C5 was detected on un-stimulated HUVEC surfaces devoid of ULVWF strings, either in the presence (FIG. 6E-F) or absence (not shown) of normal heated serum.

Results: Nonfunctional FB Reduces the Amounts of AP Components on EC-Secreted/Anchored ULVWF Strings: Functional Evidence for C3bBb (C3 Convertase) and C3bBbC3b (C5 Convertase) Assembly.

The concentrations of complement proteins in normal human serum are many-fold higher than the accumulated amounts released by the HUVECs over the 15 min time period of the previous experiments (summarized in FIG. 13). In the experiments described in this section, heated serum (diluted to 25% in PBS) was added to HUVECs during histamine stimulation. Binding intensities per micron along EC-anchored ULVWF strings was compared for C3, C5 and FB with the previous experiments using exclusively HUVEC-released complement proteins. Heating to 56° C. was necessary in order to prevent heat-labile serum ADAMTS-13 from cleaving the EC-anchored ULVWF strings prior to the addition of antibody to VWF (which also blocks ADAMTS-13-mediated VWF cleavage). The functions of C3 and C5 are unaffected by 56° C. heat. In contrast, heating to 56° C. completely inhibits the proteolytic function of FB.

The nonfunctional, structurally altered, heated form of FB exhibited an increased capacity for binding to HUVEC-anchored ULVWF strings. The binding intensities of nonfunctional FB per micron of ULVWF string in heated serum experiments were 2-fold higher than the intensities of functional FB released exclusively from HUVECs (FIG. 14). In contrast, less than half as much functional C3 from heated serum attached to ULVWF strings compared to the amounts of functional C3 attached exclusively from HUVECs (FIG. 14). These results suggest that reduced amounts of activated C3 (C3b) were generated, in the absence of functional FB, even though increased amounts of fluid-phase C3 were available in the heated serum. We conclude that heated, enzymatically-inactive serum FB bound competitively to C3b on the ULVWF strings and formed inactive C3b-FB complexes instead of active C3 convertases (C3bBb). Inactive C3b-FB complexes are incapable of the proteolytic cleavage of C3 to activated C3b that is required to attach C3b to certain surfaces (in these experiments, to HUVEC-anchored ULVWF strings).

The binding of C5 to ULVWF strings also did not increase with the addition of higher quantities of functional C5 in heated serum (FIG. 14). This is compatible with a reduced number of ULVWF string-bound C3b molecules restricting binding sites for C5 on C3b molecules adjacent to, or in, C3bBbC3b (C5 convertase) complexes. The large increase in heat-inactivated FB binding to the EC-anchored ULVWF strings may further restrict C5 binding to the ULVWF strings by sterically hindering the access of C5 to binding sites on C3b.

Therefore, the present invention is well adapted to attain the ends and advantages mentioned as well as those that are inherent therein. It should be understood, however, that the description of specific example embodiments is not intended to limit the invention to the particular forms disclosed, but on the contrary, this disclosure is to cover all modifications and equivalents as defined by the appended claims. While numerous changes may be made by those skilled in the art, such changes are encompassed within the spirit of this invention as illustrated, in part, by the appended claims.

What is claimed is:

1. A method comprising administering a composition to an individual suffering from a thrombotic microangiopathy, wherein the composition comprises a heat-inactivated complement factor B.

2. The method of claim 1 wherein the composition further comprises plasma.

3. The method of claim 2 wherein the plasma is selected from the group consisting of normal human fresh frozen plasma, a cryosupernatant fraction of fresh frozen plasma, and normal human plasma.

4. The method of claim 1 wherein the heat-inactivated complement factor B is purified heat-inactivated complement factor B.

5. A method comprising administering a composition to an individual suffering from age-related macular degeneration, wherein the composition comprises a heat-inactivated complement factor B.

6. A method comprising administering a composition to an individual suffering from a complement-mediated inflammatory disorder selected from the group consisting of lupus erythematosus, glomerulonephritis, paroxysmal nocturnal hemoglobinuria, and inflammatory bowel disease, wherein the composition comprises a heat-inactivated complement factor B.

* * * * *